(12) United States Patent
Pradeep et al.

(10) Patent No.: US 8,392,253 B2
(45) Date of Patent: *Mar. 5, 2013

(54) NEURO-PHYSIOLOGY AND NEURO-BEHAVIORAL BASED STIMULUS TARGETING SYSTEM

(75) Inventors: Anantha Pradeep, Berkeley, CA (US); Robert T. Knight, Berkeley, CA (US); Ramachandran Gurumoorthy, Berkeley, CA (US)

(73) Assignee: The Nielsen Company (US), LLC, Schaumburg, IL (US)

( * ) Notice: Subject to any disclaimer, the term of this patent is extended or adjusted under 35 U.S.C. 154(b) by 399 days.

This patent is subject to a terminal disclaimer.

(21) Appl. No.: 12/122,262

(22) Filed: May 16, 2008

(65) Prior Publication Data

US 2009/0327068 A1 Dec. 31, 2009

Related U.S. Application Data

(60) Provisional application No. 60/938,286, filed on May 16, 2007.

(51) Int. Cl.
*G06Q 30/00* (2012.01)
(52) U.S. Cl. .................. 705/14.42; 705/14.52
(58) Field of Classification Search ............... 705/14.41, 705/14.66
See application file for complete search history.

(56) References Cited

U.S. PATENT DOCUMENTS

| | | | |
|---|---|---|---|
| 2,549,836 A | 4/1951 | McIntyre et al. |
| 3,490,439 A | 1/1970 | Rolston |
| 3,572,322 A | 3/1971 | Wade |
| 3,735,753 A | 5/1973 | Pisarski |
| 3,880,144 A | 4/1975 | Coursin et al. |
| 3,901,215 A | 8/1975 | John |
| 3,998,213 A | 12/1976 | Price |
| 4,075,657 A | 2/1978 | Weinblatt |
| 4,149,716 A | 4/1979 | Scudder |
| 4,201,224 A | 5/1980 | John |
| 4,279,258 A | 7/1981 | John |
| 4,411,273 A | 10/1983 | John |
| 4,417,592 A | 11/1983 | John |
| 4,537,198 A | 8/1985 | Corbett |
| 4,557,270 A | 12/1985 | John |
| 4,610,259 A | 9/1986 | Cohen et al. |
| 4,613,951 A | 9/1986 | Chu |

(Continued)

FOREIGN PATENT DOCUMENTS

| | | |
|---|---|---|
| GB | 1374658 | 11/1974 |
| GB | 2221759 | 2/1990 |

(Continued)

OTHER PUBLICATIONS

Haq, Amber, "This is Your Brain on Advertising," Business Week, Market Research, Oct. 8, 2007, 2 pages.

(Continued)

*Primary Examiner* — Ella Colbert
*Assistant Examiner* — Scott S Trotter
(74) *Attorney, Agent, or Firm* — Hanley, Flight & Zimmerman, LLC

(57) ABSTRACT

A system performs stimulus targeting using neuro-physiological and neuro-behavioral data. Subjects are exposed to stimulus material such as marketing and entertainment materials and data is collected using mechanisms such as Electroencephalography (EEG), Galvanic Skin Response (GSR), Electrocardiograms (EKG), Electrooculography (EOG), eye tracking, and facial emotion encoding. Neuro-physiological and neuro-behavioral data collected is analyzed to select targeted stimulus materials. The targeted stimulus materials are provided to particular subjects for a variety of purposes.

23 Claims, 7 Drawing Sheets

| Dataset Data Model 301 | | | | | |
|---|---|---|---|---|---|
| Experiment Name 303 | Client Attributes 305 | Subject Pool 307 | Logistics Information 309 | Stimulus Material 311 | ... |

| Subject Attributes Data Model 315 | | | |
|---|---|---|---|
| Subject Name 317 | Demographic Attributes 319 | Contact Information 321 | ... |

| Neuro-Feedback Association Data Model 325 | | | |
|---|---|---|---|
| Experiment Protocols 327 | Modalities included 329 | Experiment Design Parameters 333 | ... |

| Data Collection Data Model 337 | | | | |
|---|---|---|---|---|
| Recording Attributes 339 | Equipment Attributes 341 | Modalities Recorded 343 | Data Storage Attributes 345 | ... |

| Preset Query Data Model 349 | | | | |
|---|---|---|---|---|
| Query Name 351 | Accessed Data Collection 353 | Access Security Attributes 355 | Refresh Attributes 357 | ... |

U.S. PATENT DOCUMENTS

| | | | |
|---|---|---|---|
| 4,632,122 A | 12/1986 | Johansson et al. | |
| 4,683,892 A | 8/1987 | Johansson et al. | |
| 4,695,879 A | 9/1987 | Weinblatt | |
| 4,736,751 A | 4/1988 | Gevins et al. | |
| 4,800,888 A | 1/1989 | Itil et al. | |
| 4,802,484 A | 2/1989 | Friedman et al. | |
| 4,846,190 A | 7/1989 | John | |
| 4,885,687 A | 12/1989 | Carey | |
| 4,894,777 A | 1/1990 | Negishi et al. | |
| 4,913,160 A | 4/1990 | John | |
| 4,955,388 A | 9/1990 | Silberstein | |
| 4,967,038 A | 10/1990 | Gevins et al. | |
| 4,987,903 A | 1/1991 | Keppel et al. | |
| 5,003,986 A | 4/1991 | Finitzo et al. | |
| 5,010,891 A | 4/1991 | Chamoun | |
| 5,038,782 A | 8/1991 | Gevins et al. | |
| 5,052,401 A | 10/1991 | Sherwin | |
| 5,083,571 A | 1/1992 | Prichep | |
| RE34,015 E | 8/1992 | Duffy | |
| 5,137,027 A | 8/1992 | Rosenfeld | |
| 5,213,338 A | 5/1993 | Brotz | |
| 5,226,177 A | 7/1993 | Nickerson | |
| 5,243,517 A * | 9/1993 | Schmidt et al. | 600/544 |
| 5,273,037 A | 12/1993 | Itil et al. | |
| 5,291,888 A | 3/1994 | Tucker | |
| 5,293,867 A | 3/1994 | Oommen | |
| 5,295,491 A | 3/1994 | Gevins | |
| 5,339,826 A | 8/1994 | Schmidt et al. | |
| 5,357,957 A | 10/1994 | Itil et al. | |
| 5,363,858 A | 11/1994 | Farwell | |
| 5,392,788 A | 2/1995 | Hudspeth | |
| 5,406,956 A | 4/1995 | Farwell | |
| 5,447,166 A | 9/1995 | Gevins | |
| 5,474,082 A | 12/1995 | Junker | |
| 5,479,934 A | 1/1996 | Imran | |
| 5,518,007 A | 5/1996 | Becker | |
| 5,537,618 A | 7/1996 | Boulton et al. | |
| 5,617,855 A | 4/1997 | Waletzky et al. | |
| 5,655,534 A | 8/1997 | Ilmoniemi | |
| 5,676,138 A | 10/1997 | Zawilinski | |
| 5,720,619 A | 2/1998 | Fisslinger | |
| 5,724,987 A | 3/1998 | Gevins et al. | |
| 5,729,205 A | 3/1998 | Kwon | |
| 5,740,035 A | 4/1998 | Cohen et al. | |
| 5,762,611 A | 6/1998 | Lewis et al. | |
| 5,771,897 A | 6/1998 | Zufrin | |
| 5,787,187 A | 7/1998 | Bouchard et al. | |
| 5,800,351 A | 9/1998 | Mann | |
| 5,812,642 A | 9/1998 | Leroy | |
| 5,817,029 A | 10/1998 | Gevins et al. | |
| 5,848,399 A | 12/1998 | Burke | |
| 5,945,863 A | 8/1999 | Coy | |
| 5,961,332 A * | 10/1999 | Joao | 434/236 |
| 5,983,129 A | 11/1999 | Cowan et al. | |
| 6,001,065 A | 12/1999 | DeVito | |
| 6,021,346 A | 2/2000 | Ryu et al. | |
| 6,052,619 A | 4/2000 | John | |
| 6,099,319 A * | 8/2000 | Zaltman et al. | 434/236 |
| 6,120,440 A * | 9/2000 | Goknar | 600/300 |
| 6,128,521 A | 10/2000 | Marro et al. | |
| 6,154,669 A | 11/2000 | Hunter et al. | |
| 6,161,030 A | 12/2000 | Levendowski et al. | |
| 6,173,260 B1 | 1/2001 | Slaney | |
| 6,175,753 B1 | 1/2001 | Menkes et al. | |
| 6,228,038 B1 | 5/2001 | Claessens | |
| 6,236,885 B1 | 5/2001 | Hunter et al. | |
| 6,254,536 B1 | 7/2001 | DeVito | |
| 6,280,198 B1 * | 8/2001 | Calhoun et al. | 434/236 |
| 6,286,005 B1 | 9/2001 | Cannon | |
| 6,289,234 B1 | 9/2001 | Mueller | |
| 6,292,688 B1 | 9/2001 | Patton | |
| 6,301,493 B1 | 10/2001 | Marro et al. | |
| 6,315,569 B1 | 11/2001 | Zaltman | |
| 6,330,470 B1 | 12/2001 | Tucker et al. | |
| 6,334,778 B1 * | 1/2002 | Brown | 434/258 |
| 6,374,143 B1 | 4/2002 | Berrang et al. | |
| 6,381,481 B1 | 4/2002 | Levendowski et al. | |
| 6,398,643 B1 | 6/2002 | Knowles et al. | |
| 6,422,999 B1 | 7/2002 | Hill | |
| 6,434,419 B1 | 8/2002 | Gevins et al. | |
| 6,453,194 B1 | 9/2002 | Hill | |
| 6,487,444 B2 | 11/2002 | Mimura | |
| 6,488,617 B1 | 12/2002 | Katz | |
| 6,510,340 B1 | 1/2003 | Jordan | |
| 6,520,905 B1 | 2/2003 | Surve et al. | |
| 6,545,685 B1 | 4/2003 | Dorbie | |
| 6,575,902 B1 | 6/2003 | Burton | |
| 6,577,329 B1 | 6/2003 | Flickner et al. | |
| 6,585,521 B1 | 7/2003 | Obrador | |
| 6,594,521 B2 | 7/2003 | Tucker | |
| 6,598,006 B1 | 7/2003 | Honda et al. | |
| 6,654,626 B2 | 11/2003 | Devlin et al. | |
| 6,662,052 B1 | 12/2003 | Sarwal et al. | |
| 6,665,560 B2 | 12/2003 | Becker et al. | |
| 6,688,890 B2 | 2/2004 | von Buegner | |
| 6,708,051 B1 | 3/2004 | Durousseau | |
| 6,712,468 B1 | 3/2004 | Edwards | |
| 6,754,524 B2 | 6/2004 | Johnson, Jr. | |
| 6,757,556 B2 | 6/2004 | Gopinathan et al. | |
| 6,788,882 B1 | 9/2004 | Geer et al. | |
| 6,792,304 B1 | 9/2004 | Silberstein | |
| 6,842,877 B2 * | 1/2005 | Robarts et al. | 715/708 |
| 6,904,408 B1 | 6/2005 | McCarthy et al. | |
| 6,950,698 B2 | 9/2005 | Sarkela et al. | |
| 6,958,710 B2 | 10/2005 | Zhang et al. | |
| 6,973,342 B1 | 12/2005 | Swanson | |
| 6,993,380 B1 | 1/2006 | Modarres | |
| 7,130,673 B2 | 10/2006 | Tolvanen-Laakso et al. | |
| 7,150,715 B2 | 12/2006 | Collura et al. | |
| 7,164,967 B2 | 1/2007 | Etienne-Cummings et al. | |
| 7,177,675 B2 | 2/2007 | Suffin et al. | |
| 7,222,071 B2 | 5/2007 | Neuhauser et al. | |
| 7,272,982 B2 | 9/2007 | Neuhauser et al. | |
| 7,286,871 B2 | 10/2007 | Cohen | |
| 7,340,060 B2 | 3/2008 | Tomkins et al. | |
| 7,391,835 B1 | 6/2008 | Gross et al. | |
| 7,408,460 B2 | 8/2008 | Crystal et al. | |
| 7,420,464 B2 | 9/2008 | Fitzgerald et al. | |
| 7,443,292 B2 | 10/2008 | Jensen et al. | |
| 7,460,827 B2 | 12/2008 | Schuster et al. | |
| 7,463,143 B2 | 12/2008 | Forr et al. | |
| 7,463,144 B2 | 12/2008 | Crystal et al. | |
| 7,471,987 B2 | 12/2008 | Crystal et al. | |
| 7,483,835 B2 | 1/2009 | Neuhauser et al. | |
| 7,496,400 B2 | 2/2009 | Hoskonen et al. | |
| 7,548,774 B2 | 6/2009 | Kurtz et al. | |
| 7,551,952 B2 | 6/2009 | Gevins et al. | |
| 7,592,908 B2 | 9/2009 | Zhang et al. | |
| 7,614,066 B2 | 11/2009 | Urdang et al. | |
| 7,623,823 B2 | 11/2009 | Zito et al. | |
| 7,636,456 B2 | 12/2009 | Collins et al. | |
| 7,650,793 B2 | 1/2010 | Jensen et al. | |
| 7,689,272 B2 | 3/2010 | Farwell | |
| 7,697,979 B2 | 4/2010 | Martinerie et al. | |
| 7,698,238 B2 | 4/2010 | Barletta et al. | |
| 7,720,351 B2 | 5/2010 | Levitan | |
| 7,729,755 B2 | 6/2010 | Laken | |
| 7,809,420 B2 | 10/2010 | Hannula et al. | |
| 7,840,248 B2 | 11/2010 | Fuchs et al. | |
| 7,840,250 B2 | 11/2010 | Tucker | |
| 7,865,394 B1 | 1/2011 | Calloway | |
| 7,892,764 B2 | 2/2011 | Xiong et al. | |
| 7,908,133 B2 | 3/2011 | Neuhauser | |
| 7,917,366 B1 | 3/2011 | Levanon et al. | |
| 7,962,315 B2 | 6/2011 | Jensen et al. | |
| 7,988,557 B2 | 8/2011 | Soderlund | |
| 8,014,847 B2 * | 9/2011 | Shastri et al. | 600/410 |
| 8,098,152 B2 | 1/2012 | Zhang et al. | |
| 8,135,606 B2 | 3/2012 | Dupree | |
| 8,165,916 B2 | 4/2012 | Hoffberg et al. | |
| 8,209,224 B2 | 6/2012 | Pradeep et al. | |
| 8,229,469 B2 | 7/2012 | Zhang et al. | |
| 8,270,814 B2 | 9/2012 | Pradeep et al. | |
| 2001/0020236 A1 | 9/2001 | Cannon | |
| 2001/0056225 A1 | 12/2001 | DeVito | |
| 2002/0065826 A1 | 5/2002 | Bell et al. | |
| 2002/0072952 A1 | 6/2002 | Hamzy et al. | |

| | | | | | | |
|---|---|---|---|---|---|---|
| 2002/0077534 A1 | 6/2002 | DuRousseau | | 2008/0001600 A1 | 1/2008 | deCharms |
| 2002/0155878 A1 | 10/2002 | Lert, Jr. et al. | | 2008/0010110 A1 | 1/2008 | Neuhauser et al. |
| 2002/0156842 A1 | 10/2002 | Signes et al. | | 2008/0027345 A1 | 1/2008 | Kumada et al. |
| 2002/0188216 A1 | 12/2002 | Kayyali et al. | | 2008/0040740 A1 | 2/2008 | Plotnick et al. |
| 2002/0188217 A1 | 12/2002 | Farwell | | 2008/0059997 A1 | 3/2008 | Plotnick et al. |
| 2002/0193670 A1 | 12/2002 | Garfield et al. | | 2008/0065468 A1 | 3/2008 | Berg et al. |
| 2003/0013981 A1* | 1/2003 | Gevins et al. ............. 600/544 | | 2008/0065721 A1 | 3/2008 | Cragun |
| 2003/0036955 A1 | 2/2003 | Tanaka et al. | | 2008/0081961 A1 | 4/2008 | Westbrook et al. |
| 2003/0059750 A1* | 3/2003 | Bindler et al. ............. 434/236 | | 2008/0082019 A1 | 4/2008 | Ludving et al. |
| 2003/0073921 A1 | 4/2003 | Sohmer et al. | | 2008/0086356 A1 | 4/2008 | Glassman et al. |
| 2003/0100998 A2 | 5/2003 | Brunner et al. | | 2008/0091512 A1 | 4/2008 | Marci et al. |
| 2003/0104865 A1 | 6/2003 | Itkis et al. | | 2008/0097854 A1 | 4/2008 | Young |
| 2003/0165270 A1 | 9/2003 | Endrikhovski et al. | | 2008/0109840 A1 | 5/2008 | Walter et al. |
| 2003/0177488 A1 | 9/2003 | Smith et al. | | 2008/0125110 A1 | 5/2008 | Ritter |
| 2003/0233278 A1 | 12/2003 | Marshall | | 2008/0147488 A1 | 6/2008 | Tunick et al. |
| 2004/0005143 A1 | 1/2004 | Tsuru et al. | | 2008/0152300 A1 | 6/2008 | Knee et al. |
| 2004/0013398 A1 | 1/2004 | Miura et al. | | 2008/0204273 A1 | 8/2008 | Crystal et al. |
| 2004/0015608 A1 | 1/2004 | Ellis et al. | | 2008/0208072 A1 | 8/2008 | Fadem et al. |
| 2004/0073129 A1 | 4/2004 | Caldwell et al. | | 2008/0214902 A1 | 9/2008 | Lee et al. |
| 2004/0092809 A1 | 5/2004 | DeCharms | | 2008/0221400 A1 | 9/2008 | Lee et al. |
| 2004/0098298 A1 | 5/2004 | Yin | | 2008/0221472 A1 | 9/2008 | Lee et al. |
| 2004/0187167 A1 | 9/2004 | Maguire et al. | | 2008/0221969 A1 | 9/2008 | Lee et al. |
| 2004/0210159 A1* | 10/2004 | Kibar ............. 600/558 | | 2008/0222670 A1 | 9/2008 | Lee et al. |
| 2004/0220483 A1 | 11/2004 | Yeo et al. | | 2008/0222671 A1 | 9/2008 | Lee et al. |
| 2004/0236623 A1 | 11/2004 | Gopalakrishnan | | 2008/0228077 A1 | 9/2008 | Wilk et al. |
| 2005/0010475 A1 | 1/2005 | Perkowski et al. | | 2008/0255949 A1 | 10/2008 | Genco et al. |
| 2005/0076359 A1 | 4/2005 | Pierson et al. | | 2008/0295126 A1 | 11/2008 | Lee et al. |
| 2005/0079474 A1 | 4/2005 | Lowe | | 2009/0024049 A1 | 1/2009 | Pradeep et al. |
| 2005/0097594 A1 | 5/2005 | O'Donnell et al. | | 2009/0024447 A1 | 1/2009 | Pradeep et al. |
| 2005/0107716 A1 | 5/2005 | Eaton et al. | | 2009/0024448 A1 | 1/2009 | Pradeep et al. |
| 2005/0143629 A1 | 6/2005 | Farwell | | 2009/0024449 A1 | 1/2009 | Pradeep et al. |
| 2005/0154290 A1 | 7/2005 | Langleben | | 2009/0024475 A1 | 1/2009 | Pradeep et al. |
| 2005/0177058 A1 | 8/2005 | Sobell | | 2009/0025023 A1 | 1/2009 | Pradeep et al. |
| 2005/0197590 A1 | 9/2005 | Osorio et al. | | 2009/0030287 A1 | 1/2009 | Pradeep et al. |
| 2005/0203798 A1 | 9/2005 | Jensen et al. | | 2009/0030303 A1 | 1/2009 | Pradeep et al. |
| 2005/0223237 A1 | 10/2005 | Barletta et al. | | 2009/0030717 A1 | 1/2009 | Pradeep et al. |
| 2005/0227233 A1* | 10/2005 | Buxton et al. ............. 435/6 | | 2009/0030930 A1 | 1/2009 | Pradeep et al. |
| 2005/0240956 A1 | 10/2005 | Smith et al. | | 2009/0036755 A1 | 2/2009 | Pradeep et al. |
| 2005/0272017 A1 | 12/2005 | Neuhauser et al. | | 2009/0036756 A1 | 2/2009 | Pradeep et al. |
| 2005/0273017 A1 | 12/2005 | Gordon | | 2009/0037575 A1 | 2/2009 | Crystal et al. |
| 2005/0273802 A1 | 12/2005 | Crystal et al. | | 2009/0062629 A1 | 3/2009 | Pradeep et al. |
| 2005/0288954 A1 | 12/2005 | McCarthy et al. | | 2009/0062680 A1 | 3/2009 | Sandford |
| 2005/0289582 A1 | 12/2005 | Tavares et al. | | 2009/0062681 A1 | 3/2009 | Pradeep et al. |
| 2006/0003732 A1 | 1/2006 | Neuhauser et al. | | 2009/0063255 A1 | 3/2009 | Pradeep et al. |
| 2006/0035707 A1 | 2/2006 | Nguyen et al. | | 2009/0063256 A1 | 3/2009 | Pradeep et al. |
| 2006/0053110 A1 | 3/2006 | McDonald et al. | | 2009/0070798 A1 | 3/2009 | Lee et al. |
| 2006/0093998 A1 | 5/2006 | Vertegaal | | 2009/0082643 A1 | 3/2009 | Pradeep et al. |
| 2006/0111044 A1 | 5/2006 | Keller | | 2009/0083129 A1 | 3/2009 | Pradeep et al. |
| 2006/0111644 A1 | 5/2006 | Guttag et al. | | 2009/0088610 A1 | 4/2009 | Lee et al. |
| 2006/0129458 A1 | 6/2006 | Maggio | | 2009/0112077 A1 | 4/2009 | Nguyen et al. |
| 2006/0167376 A1 | 7/2006 | Viirre et al. | | 2009/0253996 A1 | 10/2009 | Lee et al. |
| 2006/0168613 A1 | 7/2006 | Wood et al. | | 2009/0328089 A1 | 12/2009 | Pradeep et al. |
| 2006/0168630 A1 | 7/2006 | Davies | | 2010/0004977 A1 | 1/2010 | Marci et al. |
| 2006/0256133 A1 | 11/2006 | Rosenberg | | 2010/0022821 A1 | 1/2010 | Dubi et al. |
| 2006/0257834 A1 | 11/2006 | Lee et al. | | 2010/0060300 A1 | 3/2010 | Mueller et al. |
| 2006/0259360 A1 | 11/2006 | Flinn et al. | | 2010/0125219 A1 | 5/2010 | Harris et al. |
| 2006/0293921 A1 | 12/2006 | McCarthy et al. | | 2010/0145215 A1 | 6/2010 | Pradeep et al. |
| 2007/0048707 A1 | 3/2007 | Caamano et al. | | 2010/0183279 A1 | 7/2010 | Pradeep et al. |
| 2007/0055169 A1 | 3/2007 | Lee et al. | | 2010/0186031 A1 | 7/2010 | Pradeep et al. |
| 2007/0060831 A1 | 3/2007 | Le et al. | | 2010/0186032 A1 | 7/2010 | Pradeep et al. |
| 2007/0066874 A1 | 3/2007 | Cook | | 2010/0198042 A1 | 8/2010 | Popescu et al. |
| 2007/0066915 A1 | 3/2007 | Frei et al. | | 2010/0214318 A1 | 8/2010 | Pradeep et al. |
| 2007/0066916 A1 | 3/2007 | Lemos | | 2010/0215289 A1 | 8/2010 | Pradeep et al. |
| 2007/0067007 A1 | 3/2007 | Schulman et al. | | 2010/0218208 A1 | 8/2010 | Holden |
| 2007/0078706 A1 | 4/2007 | Datta et al. | | 2010/0249538 A1 | 9/2010 | Pradeep et al. |
| 2007/0079331 A1 | 4/2007 | Datta et al. | | 2010/0249636 A1 | 9/2010 | Pradeep et al. |
| 2007/0106170 A1 | 5/2007 | Dunseath, Jr. et al. | | 2010/0250325 A1 | 9/2010 | Pradeep et al. |
| 2007/0135727 A1 | 6/2007 | Virtanen et al. | | 2010/0257052 A1 | 10/2010 | Zito et al. |
| 2007/0135728 A1 | 6/2007 | Snyder et al. | | 2010/0325660 A1 | 12/2010 | Holden |
| 2007/0225585 A1 | 9/2007 | Washbon et al. | | 2011/0046473 A1 | 2/2011 | Pradeep et al. |
| 2007/0225674 A1 | 9/2007 | Molnar et al. | | 2011/0046502 A1 | 2/2011 | Pradeep et al. |
| 2007/0226760 A1 | 9/2007 | Neuhauser et al. | | 2011/0046503 A1 | 2/2011 | Pradeep et al. |
| 2007/0235716 A1 | 10/2007 | Delic et al. | | 2011/0046504 A1 | 2/2011 | Pradeep et al. |
| 2007/0238945 A1 | 10/2007 | Delic et al. | | 2011/0047121 A1 | 2/2011 | Pradeep et al. |
| 2007/0250846 A1 | 10/2007 | Swix et al. | | 2011/0059422 A1 | 3/2011 | Masaoka |
| 2007/0265507 A1 | 11/2007 | de Lemos | | 2011/0105937 A1 | 5/2011 | Pradeep et al. |
| 2007/0294132 A1 | 12/2007 | Zhang et al. | | 2011/0106621 A1 | 5/2011 | Pradeep et al. |
| 2007/0294705 A1 | 12/2007 | Gopalakrishnan | | 2011/0106750 A1 | 5/2011 | Pradeep et al. |
| 2007/0294706 A1 | 12/2007 | Neuhauser et al. | | 2011/0119124 A1 | 5/2011 | Pradeep et al. |

| | | | |
|---|---|---|---|
| 2011/0119129 | A1 | 5/2011 | Pradeep et al. |
| 2011/0208515 | A1 | 8/2011 | Neuhauser |
| 2011/0237971 | A1 | 9/2011 | Pradeep et al. |
| 2011/0248729 | A2 | 10/2011 | Mueller et al. |
| 2011/0270620 | A1 | 11/2011 | Pradeep et al. |
| 2011/0276504 | A1 | 11/2011 | Pradeep et al. |
| 2011/0282231 | A1 | 11/2011 | Pradeep et al. |
| 2011/0282232 | A1 | 11/2011 | Pradeep et al. |
| 2011/0282749 | A1 | 11/2011 | Pradeep et al. |
| 2012/0036004 | A1 | 2/2012 | Pradeep et al. |
| 2012/0036005 | A1 | 2/2012 | Pradeep et al. |
| 2012/0054018 | A1 | 3/2012 | Pradeep et al. |
| 2012/0072289 | A1 | 3/2012 | Pradeep et al. |
| 2012/0108995 | A1 | 5/2012 | Pradeep et al. |
| 2012/0114305 | A1 | 5/2012 | Holden |
| 2012/0245978 | A1 | 9/2012 | Crystal et al. |

FOREIGN PATENT DOCUMENTS

| | | |
|---|---|---|
| WO | 95-18565 | 7/1995 |
| WO | 97/17774 | 5/1997 |
| WO | 97/40745 | 11/1997 |
| WO | 97/41673 | 11/1997 |
| WO | 02-00241 | 12/2002 |
| WO | 02-02238 | 12/2002 |
| WO | 2004/049225 | 6/2004 |
| WO | 2008/121651 | 10/2008 |
| WO | 2008/137579 | 11/2008 |
| WO | 2008/154410 | 12/2008 |
| WO | 2009/018374 | 2/2009 |
| WO | 2009/052833 | 4/2009 |

OTHER PUBLICATIONS

Barcelo, Francisco, et al., "Prefrontal Modulation of Visual Processing in Humans," Nature Neuroscience, vol. 3, No. 4, Apr. 2000, pp. 399-403.
Canolty, R.T., et al., "High Gamma Power Is Phase-Locked to Theta Oscillations in Human Neocortex," Science, vol. 313, Sep. 15, 2006, pp. 1626-1628.
Engel, Andreas, et al., "Dynamic Predictions: Oscillations and Synchrony in Top-Down Processing," Macmillan Magazines Ltd, vol. 2, Oct. 2001, pp. 704-716.
Fries, Pascal, "A Mechanism for Cognitive Dynamics: Neuronal Communication Through Neuronal Coherence," Trends in Cognitive Sciences, vol. 9, No. 10, Oct. 2005, p. 474-480.
Gazzaley, Adam, et al., "Top-down Enhancement and Suppression of the Magnitude and Speed of Neural Activity," Journal of Cognitive Neuroscience, vol. 17, No. 3, pp. 507-517.
Hartikainen, Kaisa, et al., "Emotionally Arousing Stimuli Compete with Attention to Left Hemispace," Editorial Manager(tm) for NeuroReport, Manuscipt Draft, Manuscript No. NR-D-07-5935R1, submitted Sep. 8, 2007, 26 pages.
Knight, Robert T., "Contribution of Human Hippocampal Region to Novelty Detection," Nature, vol. 383, Sep. 19, 1996, p. 256-259.
Knight Robert T., "Decreased Response to Novel Stimuli After Prefrontal Lesions in Man," Electroencephalography and Clinical Neurophysiology, vol. 59, 1984, pp. 9-20.
Miltner, Wolfgang H.R., et al., "Coherence of Gamma-band EEG Activity as a Basis for Associative Learning," Nature, vol. 397, Feb. 4, 1999, pp. 434-436.
Final Rejection, issued by the United States Patent and Trademark Office in connection with U.S. Appl. No. 12/056,211, on Jul. 8, 2011, 16 pages.
Office Action, issued by the United States Patent and Trademark Office in connection with U.S. Appl. No. 12/056,211, on Jan. 7, 2011, 19 pages.
Office Action issued by the United States Patent and Trademark Office in connection with U.S. Appl. No. 12/056,221, on Apr. 15, 2011, 24 pages.
Final Rejection, issued by the United States Patent and Trademark Office in connection with U.S. Appl. No. 12/113,863, on Jun. 9, 2011, 12 pages.
Office Action, issued by the United States Patent and Trademark Office in connection with U.S. Appl. No. 12/113,863, on Dec. 27, 2010, 15 pages.
Final Rejection, issued by the United States Patent and Trademark Office in connection with U.S. Appl. No. 12/113,870, on Apr. 21, 2011, 10 pages.
Office Action, issued by the United States Patent and Trademark Office in connection with U.S. Appl. No. 12/113,870, on Dec. 3, 2010, 12 pages.
Office Action, issued by the United States Patent and Trademark Office in connection with U.S. Appl. No. 12/122,240, on Jun. 10, 2011, 12 pages.
Final Rejection, issued by the United States Patent and Trademark Office in connection with U.S. Appl. No. 12/135,066, on Jan. 21, 2011, 16 pages.
Office Action, issued by the United States Patent and Trademark Office in connection with U.S. Appl. No. 12/135,066, on Oct. 28, 2010, 14 pages.
Notice of Panel Decision from Pre-Appeal Brief Review, issued by the United States Patent and Trademark Office in connection with U.S. Appl. No. 12/135,066, on May 31, 2011, 2 pages.
Office Action, issued by the United States Patent and Trademark Office in connection with U.S. Appl. No. 12/135,074, on Dec. 23, 2010, 14 pages.
Final Rejection, issued by the United States Patent and Trademark Office in connection with U.S. Appl. No. 12/135,074, on Jun. 9, 2011, 10 pages.
Final Rejection, issued by the United States Patent and Trademark Office in connection with U.S. Appl. No. 12/182,874, on Jul. 7, 2011, 14 pages.
Office Action, issued by the United States Patent and Trademark Office in connection with U.S. Appl. No. 12/182,874, on Dec. 27, 2010, 17 pages.
Office Action, issued by the United States Patent and Trademark Office in connection with U.S. Appl. No. 12/199,557, on Dec. 27, 2010, 14 pages.
Final Rejection, issued by the United States Patent and Trademark Office in connection with U.S. Appl. No. 12/199,557, on Jun. 9, 2011, 12 pages.
Final Rejection, issued by the United States Patent and Trademark Office in connection with U.S. Appl. No. 12/199,583, on Jun. 21, 2011, 14 pages.
Office Action, issued by the United States Patent and Trademark Office in connection with U.S. Appl. No. 12/199,583, on Dec. 27, 2010, 17 pages.
Final Rejection, issued by the United States Patent and Trademark Office in connection with U.S. Appl. No. 12/199,596, on Jun. 14, 2011, 13 pages.
Office Action, issued by the United States Patent and Trademark Office in connection with U.S. Appl. No. 12/199,596, on Dec. 27, 2010, 17 pages.
Final Rejection, issued by the United States Patent and Trademark Office in connection with U.S. Appl. No. 12/200,813, on Jul. 6, 2011, 13 pages.
Office Action, issued by the United States Patent and Trademark Office in connection with U.S. Appl. No. 12/200,813, on Dec. 27, 2010, 14 pages.
Office Action, issued by the United States Patent and Trademark Office in connection with U.S. Appl. No. 12/234,372, on Jun. 7, 2011, 10 pages.
Final Rejection, issued by the United States Patent and Trademark Office in connection with U.S. Appl. No. 12/135,069, on Feb. 17, 2011, 32 pages.
Office Action, issued by the United States Patent and Trademark Office in connection with U.S. Appl. No. 12/135,069, on Oct. 29, 2010, 21 pages.
Office Action, issued by the United States Patent and Trademark Office in connection with U.S. Appl. No. 12/357,315, on May 4, 2011, 9 pages.
Office Action, issued by the United States Patent and Trademark Office in connection with U.S. Appl. No. 12/410,380, on Jun. 7, 2011, 9 pages.
Office Action, issued by the United States Patent and Trademark Office in connection with U.S. Appl. No. 12/413,297, on Jul. 18, 2011, 9 pages.

Office Action, issued by the United States Patent and Trademark Office in connection with U.S. Appl. No. 12/608,685, on Jul. 12, 2011, 15 pages.
Office Action, issued by the United States Patent and Trademark Office in connection with U.S. Appl. No. 12/056,190, on Aug. 10, 2011, 28 pages.
Office Action, issued by the United States Patent and Trademark Office in connection with U.S. Appl. No. 12/357,322, on Aug. 23, 2011, 12 pages.
Office Action, issued by the United States Patent and Trademark Office in connection with U.S. Appl. No. 12/135,069, on Aug. 26, 2011, 33 pages.
Restriction Requirement, issued by the United States Patent and Trademark Office in connection with U.S. Appl. No. 12/122,253, on Sep. 2, 2011, 7 pages.
Office Action, issued by the United States Patent and Trademark Office in connection with U.S. Appl. No. 12/410,372, on Sep. 12, 2011, 12 pages.
Restriction Requirement, issued by the United States Patent and Trademark Office in connection with U.S. Appl. No. 12/182,851, on Sep. 12, 2011, 7 pages.
Office Action, issued by the United States Patent and Trademark Office in connection with U.S. Appl. No. 12/135,066, on Sep. 29, 2011, 37 pages.
Restriction Requirement, issued by the United States Patent and Trademark Office in connection with U.S. Appl. No. 12/056,225, on Oct. 3, 2011, 6 pages.
Office Action, issued by the United States Patent and Trademark Office in connection with U.S. Appl. No. 12/234,388, on Oct. 12, 2011, 27 pages.
Office Action, issued by the United States Patent and Trademark Office in connection with U.S. Appl. No. 12/234,372, on Oct. 13, 2011, 22 pages.
Office Action, issued by the United States Patent and Trademark Office in connection with U.S. Appl. No. 12/410,380, on Oct. 19, 2011, 21 pages.
Final Rejection, issued by the United States Patent and Trademark Office in connection with U.S. Appl. No. 12/357,315, on Oct. 26, 2011, 13 pages.
Final Rejection, issued by the United States Patent and Trademark Office in connection with U.S. Appl. No. 12/122,240, on Oct. 27, 2011, 13 pages.
International Preliminary Report on Patentability, issued by the International Bureau of WIPO in connection with International Application No. PCT/US08/058264, on Sep. 29, 2009, 1 page.
International Search Report, issued by the International Searching Authority in connection with International Application No. PCT/US08/058264, on Aug. 1, 2008, 2 pages.
Written Opinion, issued by the International Searching Authority in connection with International Application No. PCT/US08/058264, on Aug. 1, 2008, 5 pages.
International Preliminary Report on Patentability, issued by the International Bureau of WIPO in connection with International Application No. PCT/US08/062273, on Nov. 3, 2009, 1 page.
International Search Report, issued by the International Searching Authority in connection with International Application No. PCT/US08/062273, on Sep. 5, 2008, 2 pages.
Written Opinion, issued by the International Searching Authority in connection with International Application No. PCT/US08/062273, on Sep. 5, 2008, 4 pages.
International Preliminary Report on Patentability, issued by the International Bureau of WIPO in connection with International Application No. PCT/US08/062275, on Nov. 3, 2009, 1 page.
International Search Report, issued by the International Bureau in connection with International Application No. PCT/US08/062275, on Sep. 22, 2008, 2 pages.
Written Opinion, issued by the International Bureau in connection with International Application No. PCT/US08/062275, on Sep. 22, 2008, 6 pages.
International Preliminary Report on Patentability, issued by the International Bureau of WIPO in connection with International Application No. PCT/US08/063984, on Nov. 17, 2009, 1 page.
International Search Report, issued by the International Bureau in connection with International Application No. PCT/US08/063984, on Sep. 29, 2008, 3 pages.
Written Opinion, issued by the International Bureau in connection with International Application No. PCT/US08/063984, on Sep. 29, 2008, 4 pages.
International Preliminary Report on Patentability, issued by the International Bureau of WIPO in connection with International Application No. PCT/US08/063989, on Nov. 17, 2009, 1 page.
International Search Report, issued by the International Bureau in connection with International Application No. PCT/US08/063989, on Jul. 17, 2008, 2 pages.
Written Opinion, issued by the International Bureau in connection with International Application No. PCT/US08/063989, on Jul. 17, 2008, 4 pages.
International Preliminary Report on Patentability, issued by the International Bureau of WIPO in connection with International Application No. PCT/US08/066166, on Dec. 7, 2009, 1 page.
International Search Report, issued by the International Bureau in connection with International Application No. PCT/US08/066166, on Aug. 25, 2008, 2 pages.
Written Opinion, issued by the International Bureau in connection with International Application No. PCT/US08/066166, on Aug. 25, 2008, 6 pages.
International Preliminary Report on Patentability, issued by the International Bureau of WIPO in connection with International Application No. PCT/US08/071639, on Feb. 2, 2010, 1 page.
International Search Report, issued by the International Bureau in connection with International Application No. PCT/US08/071639, on Oct. 22, 2008, 3 pages.
Written Opinion, issued by the International Bureau in connection with International Application No. PCT/US08/071639, on Oct. 22, 2008, 4 pages.
International Preliminary Report on Patentability, issued by the International Bureau of WIPO in connection with International Application No. PCT/US08/074467, on Mar. 2, 2010, 1 page.
International Search Report, issued by the International Bureau in connection with International Application No. PCT/US08/074467, on Nov. 17, 2008, 2 pages.
Written Opinion, issued by the International Bureau in connection with International Application No. PCT/US08/074467, on Nov. 17, 2008, 4 pages.
International Preliminary Report of Patentability, issued by the International Bureau in connection with International Application No. PCT/US10/021535, on Jul. 26, 2011, 1 page.
International Search Report, issued by the International Bureau in connection with International Application No. PCT/US10/021535, on Mar. 23, 2010, 3 pages.
Written Opinion, issued by the International Bureau in connection with International Application No. PCT/US10/021535, on Mar. 23, 2010, 4 pages.
International Preliminary Report of Patentability, issued by the International Bureau in connection with International Application No. PCT/US09/065368, on Jun. 23, 2011, 2 pages.
International Search Report, issued by the International Bureau in connection with International Application No. PCT/US09/065368, on Jan. 21, 2010, 3 pages.
Written Opinion, issued by the International Bureau in connection with International Application No. PCT/US09/065368, on Jan. 21, 2010, 7 pages.
Extended European Search Report, issued by the European Patent Office in connection with European Application No. 08744383.4-2221/2130146, on Jul. 27, 2011, 6 pages.
Extended European Search Report, issued by the European Patent Office in connection with European Application No. 10173095.0/2221, on Dec. 17, 2010, 3 pages.
Extended European Search Report, issued by the European Patent Office in connection with European Application No. 10189294.1-2221, on Mar. 21, 2011, 7 pages.
First Office Action, issued by the State Intellectual Property Office of P.R. China in connection with Patent Application No. 200880104982.1, on Jan. 25, 2011, 15 pages.

First Office Action, issued by the State Intellectual Property Office of P.R. China in connection with Patent Application No. 200880101 5007, on May 25, 2011, 8 pages.

First Office Action, issued by the State Intellectual Property Office of P.R. China in connection with Patent Application No. 200880019166.0, on Jul. 22, 2011, 16 pages.

Decision of Rejection, issued by the State Intellectual Property Office of P.R. China in connection with Patent Application No. 200880104982.1, on Sep. 23, 2011, 10 pages.

Edgar, et al., "Digital Filters in ERP Research," in Event-Related Potentials: A Methods Handbook pp. 85-113, (Todd C. Handy, ed., 2005), 15 pages.

Simon-Thomas, et al, "Behavioral and Electrophysiological Evidence of a Right Hemisphere Bias for the Influence of Negative Emotion on Higher Cognition," Journal of Cognitive Neuroscience, pp. 518-529, Massachusetts Institute of Technology (2005), 12 pages.

Friedman, et al., "Event-Related Potential (ERP) Studies of Memory Encoding and Retrieval: A Selective Review," Microscopy Research and Technique 51:6-26, Wiley-Less, Inc. (2000), 23 pages.

Gaillard, "Problems and Paradigms in ERP Research," Biological Psychology, Elsevier Science Publisher B.V. (1988), 10 pages.

Hopf, et al., "Neural Sources of Focused Attention in Visual Search," Cerebral Cortex, 10:1233-1241, Oxford University Press, (Dec. 2000), 9 pages.

Swick, et al., "Contributions of Prefrontal Cortex to Recognition Memory: Electrophysiological and Behavioral Evidence," Neuropsychology, vol. 13, No. 2, pp. 155-170, American Psychological Association, Inc. (1999), 16 pages.

Luck, et al., "The sped of visual attention in schizophrenia: Electrophysiological and behavioral evidence," Schizophrenia Research, pp. 174-195, Elsevier B.V. www.sciencedirect.com, (2006), 22 pages.

Makeig, et al., "Mining event-related brain dynamics," Trends in Cognitive Sciences, vol. 8, No. 5, (May 2004), www.sciencedirect.com, 7 pages.

Herrmann, et al., "Mechanisms of human attention: event-related potentials and oscillations," Neuroscience and Biobehavioral Reviews, pp. 465-476, Elsevier Science Ltd., www.elsvevier.com/locate/neubiorev, (2001), 12 pages.

Paller, et al., "Validating neural correlates of familiarity," Trends in Cognitive Sciences, vol. 11, No. 6, www.sciencedirect.com, (May 2, 2007), 8 pages.

Picton, et al., "Guidelines for using human event-related potentials to study cognition: Recording standards and publication criteria," Psychophysiology, pp. 127-152, Society for Psychophysiological Research, (2000), 26 pages.

Yamaguchi, et al., "Rapid-Prefrontal—Hippocampal Habituation to Novel Events," The Journal of Neuroscience, pp. 5356-5363, Society for Neuroscience, (Apr. 29, 2004), 8 pages.

Rugg, et al., "Event-related potentials and recognition memory," Trends in Cognitive Sciences, vol. 11, No. 6, www.sciencedirect.com, (May 3, 2007), 7 pages.

Rugg, et al., "The ERP and cognitive psychology: conceptual issues," (Sep. 1996), 7 pages.

Spencer, "Averaging, Detection, and Classification of Single-Trial ERPs," in Event-Related Potentials: A Methods Handbook, pp. 209-227, (Todd C. Handy, ed., 2005), 10 pages.

Srinivasan, "High-Resolution EEG: Theory and Practice," in Event-Related Potentials: A Methods Handbook, pp. 167-188, (Todd C. Handy, ed., 2005), 12 pages.

Taheri, et al., "A dry electrode for EEG recording," Electroencephalography and clinical Neurophysiology, pp. 376-383, Elsevier Science Ireland Ltd. (1994), 8 pages.

Talsma, et al., "Methods for the Estimation and Removal of Artifacts and Overlap in ERP Waveforms," in Event-Related Potentials: A Methods Handbook, pp. 115-148, (Todd C. Handy, ed., 2005), 22 pages.

Davidson, et al., "The functional neuroanatomy of emotion and affective style," Trends in Cognitive Sciences, vol. 3, No. 1, (Jan. 1999), 11 pages.

Vogel, et al., "Electrophysiological Evidence for a Postperceptual Locus of Suppression During the Attentional Blink," Journal of Experimental Psychology: Human Perception and Performance, vol. 24, No. 6, pp. 1656-1674, (1998), 19 pages.

Rizzolatti et al., "The Mirror-Neuron System," Annu. Rev. Neurosci., vol. 27, pp. 169-192, (Mar. 5, 2004), 30 pages.

Woldorf, "Distortion of ERP averages due to overlap from temporally adjacent ERPs: Analysis and correction," Psychophysiology, Society for Psychophysiological Research, Cambridge University Press (1993), 22 pages.

Woodman, et al., "Serial Deployment of Attention During Visual Search," Journal of Experimental Psychology: Human Perception and Performance, vol. 29, No. 1, pp. 121-138, American Physiological Association (2003), 18 pages.

Knight, et al., "Prefrontal cortex regulates inhibition and excitation in distributed neural networks," Acta Psychologica vol. 101, pp. 159-178, Elsevier (1999), 20 pages.

Buschman, et al., "Top-Down versus Bottom-Up Control of Attention in the Prefrontal and posterior Parietal Cortices," Science, vol. 315, www.sciencemag.org/cgi/content/full/315/5820/1860, American Association for the Advancement of Science, (2007), 4 pages.

D'Esposito, "From cognitive to neural models of working memory," Phil. Trans. R. Soc. B, doi: 10.1098/rstb.2007.2086, (Mar. 30, 2007), 12 pages.

Dien, et al., "Application of Repeated Measures ANOVA to High-Dens Dataset: A Review and Tutorial," in Event-Related Potentials: A Methods Handbook pp. 57-82, (Todd C. Handy, ed., 2005), 14 pages.

Ambler, "Salience and Choice: Neural Correlates of Shopping Decisions," Psychology & Marketing, vol. 21, No. 4, p. 247-261, Wiley Periodicals, Inc., doi: 10.1002/mar20004, (Apr. 2004), 16 pages.

Hazlett, et al., "Emotional Response to Television Commercials: Facial EMG vs. Self-Report," Journal of Advertising Research, (Apr. 1999), 17 pages.

Makeig, et al., "Dynamic Brain Sources of Visual Evoked Responses," Science, vol. 295, www.sciencemag.org, (Jan. 25, 2002), 5 pages.

Lewis et al., "Market Researchers make Increasing use of Brain Imaging," ACNR, vol. 5, No. 3, pp. 36-37, (Jul./Aug. 2005), 2 pages.

Sutherland, "Neuromarketing: What's it all about?" Retrieved from Max Sutherland's Weblog on Aug. 23, 2011, htip://www.sutherlandsurvey.com/Column_pages/Neuromarketing_whats_it_all_about.htm, (Mar. 2007), 5 pages.

Aaker et al., "Warmth in Advertising: Measurement, Impact, and Sequence Effects," Journal of Consumer Research, vol. 12, No. 4, pp. 365-381, (Mar. 1986), 17 pages.

Belch et al., "Psychophysiological and cognitive Response to Sex in Advertising," Advances in Consumer Research, vol. 9, pp. 424-427, (1982), 6 pages.

Ruchkin et al., "Modality-specific processing streams in verbal working memory: evidence from spatio-temporal patterns of brain activity," Cognitive Brain Research, vol. 6, pp. 95-113, Elsevier, (1997), 19 pages.

Page et al., "Cognitive Neuroscience, Marketing and Research," Congress 2006—Foresight—The Predictive Power of Research Conference Papers, ESOMAR Publications, (Sep. 17, 2006), 25 pages.

Braeutigam, "Neuroeconomics-From neural systems to economic behavior," Brain Research Bulletin, vol. 67, pp. 355-360, Elsevier, (2005), 6 pages.

Lee et al., "What is 'neuromarketing'? A discussion and agenda for future research," International Journal of Psychophysiology, vol. 63, pp. 199-204, Elsevier (2006), 6 pages.

Crawford et al., "Self-generated happy and sad emotions in low and highly hypnotizable persons during waking and hypnosis: laterality and regional EEG activity differences," International Journal of Psychophysiology, vol. 24, pp. 239-266, (Dec. 1996), 28 pages.

Desmet, "Measuring Emotion: Development and Application of an Instrument to Measure Emotional Responses to Products," to be published in Funology: From Usability to Enjoyment, pp. 111-123, Kluwer Academic Publishers, (Blythe et al., eds., 2004), 13 pages.

Bagozzi et al., "The Role of Emotions in Marketing," Journal of the Academy of Marketing Science, vol. 27, No. 2, pp. 184-206, Academy of Marketing Science (1999), 23 pages.

Blakeslee, "If You Have a 'Buy Button' in Your Brain, What Pushes It?" The New York Times, www.nytimes.com, (Oct. 19, 2004), 3 pages.

Osborne, "Embedded Watermarking for image Verification in Telemedicine," Thesis submitted for the degree of Doctor of Philosophy, Electrical and Electronic Engineering, University of Adelaide (2005), 219 pages.

Nielsen, "Neuroinformatics in Functional Neuroimaging," Informatics and Mathematical Modeling, Technical University of Denmark, (Aug. 30, 2002), 241 pages.

Arousal in Sport, in Encyclopedia of Applied Psychology, vol. 1, p. 159, retrieved from Google Books, (Spielberger, ed., Elsevier Academic Press, 2004), 1 page.

Ziegenfuss, "Neuromarketing: Advertising Ethical & Medical Technology," The Brownstone Journal, vol. XII, Boston University, pp. 69-73, (May 2005), 5 pages.

Lekakos, "Personalized Advertising Services Through Hybrid Recommendation Methods: The Case of Digital Interactive Television," Department of Informatics, Cyprus University, (2004), 11 pages.

Ambler et al., "Ads on the Brain; A Neuro-Imaging Comparison of Cognitive and Affective Advertising Stimuli," London Business School, Centre for Marketing Working Paper, No. 00-902, (Mar. 2000), 23 pages.

U.S. Appl. No. 13/045,457, filed Mar. 10, 2011, (unpublished).
U.S. Appl. No. 12/778,810, filed May 12, 2010, (unpublished).
U.S. Appl. No. 12/778,828, filed May 12, 2010, (unpublished).
U.S. Appl. No. 13/104,821, filed May 10, 2011, (unpublished).
U.S. Appl. No. 13/104,840, filed May 10, 2011, (unpublished).
U.S. Appl. No. 12/853,197, filed Aug. 9, 2010, (unpublished).
U.S. Appl. No. 12/884,034, filed Sep. 16, 2010, (unpublished).
U.S. Appl. No. 12/868,531, filed Aug. 25, 2010, (unpublished).
U.S. Appl. No. 12/913,102, filed Oct. 27, 2010, (unpublished).
U.S. Appl. No. 12/853,213, filed Aug. 9, 2010, (unpublished).
U.S. Appl. No. 13/105,774, filed May 11, 2011, (unpublished).

Final Rejection, issued by the United States Patent and Trademark Office in connection with U.S. Appl. No. 12/056,221, on Nov. 28, 2011, 44 pages.

Office Action, issued by the United States Patent and Trademark Office in connection with U.S. Appl. No. 12/113,863, on Dec. 22, 2011, 17 pages.

Office Action, issued by the United States Patent and Trademark Office in connection with U.S. Appl. No. 12/135,074, on Dec. 22, 2011, 16 pages.

Office Action, issued by the United States Patent and Trademark Office in connection with U.S. Appl. No. 12/199,557, on Dec. 22, 2011, 17 pages.

Office Action, issued by the United States Patent and Trademark Office in connection with U.S. Appl. No. 12/199,596, on Dec. 22, 2011, 15 pages.

Office Action, issued by the United States Patent and Trademark Office in connection with U.S. Appl. No. 12/200,813, on Dec. 22, 2011, 18 pages.

Extended European Search Report, issued by the European Patent Office in connection with European Application No. 11006934.1-2221, on Oct. 25, 2011, 5 pages.

Office Action, issued by the United States Patent and Trademark Office in connection with U.S. Appl. No. 12/199,583, on Dec. 29, 2011, 18 pages.

Final Rejection, issued by the United States Patent and Trademark Office in connection with U.S. Appl. No. 12/410,372, on Jan. 3, 2012, 10 pages.

Final Rejection, issued by the United States Patent and Trademark Office in connection with U.S. Appl. No. 12/413,297, on Jan. 4, 2012, 10 pages.

Office Action, issued by the United States Patent and Trademark Office in connection with U.S. Appl. No. 12/608,660, on Dec. 7, 2011, 43 pages.

Office Action, issued by the United States Patent and Trademark Office in connection with U.S. Appl. No. 12/868,531, on Mar. 1, 2012, 6 pages.

Office Action, issued by the United States Patent and Trademark Office in connection with U.S. Appl. No. 12/182,851, on Mar. 12, 2012, 14 pages.

Office Action, issued by the United States Patent and Trademark Office in connection with U.S. Appl. No. 12/608,685, on Mar. 29, 2012, 17 pages.

Office Action, issued by the United States Patent and Trademark Office in connection with U.S. Appl. No. 12/846,242, on Mar. 29, 2012, 15 pages.

Office Action, issued by the United States Patent and Trademark Office in connection with U.S. Appl. No. 12/234,388, on Apr. 6, 2012, 6 pages.

Office Action, issued by the United States Patent and Trademark Office in connection with U.S. Appl. No. 12/357,315, on Apr. 9, 2012, 17 pages.

Office Action, issued by the United States Patent and Trademark Office in connection with U.S. Appl. No. 12/544,958, on May 2, 2012, 14 pages.

English Translation of Office Action, issued by the Israel Patent Office in connection with Patent Application No. 203176, on Feb. 21, 2012, 2 pages.

English Translation of Office Action, issued by the Israel Patent Office in connection with Patent Application No. 203177, on Mar. 1, 2012, 2 pages.

Second Office Action, issued by the State Intellectual Property Office of P.R. China in connection with Patent Application No. 200880101500.7, on Apr. 5, 2012, 5 pages.

Padgett et al., "Categorical Perception in Facial Emotion Classification," In Proceedings of the 18th Annual Conference of the Cognitive Science Society, pp. 249-253 (1996), 5 pages.

de Gelder et al., "Categorical Perception of Facial Expressions: Categories and their Internal Structure," Cognition and Emotion, vol. 11(1), pp. 1-23 (1997), 23 pages.

Bimler et al., "Categorical perception of facial expressions of emotion: Evidence from multidimensional scaling," Cognition and Emotion, vol. 15(5), pp. 633-658 (Sep. 2001), 26 pages.

Newell et al., "Categorical perception of familiar objects," Cognition, vol. 85, Issue 2, pp. 113-143 (Sep. 2002), 31 pages.

Meriam Webster Online Dictionary, Definition of Virtual Reality, available at http://www.meriam-webster.com/dictionary/virtual%20reality, 2 page.

Griss et al., "Characterization of micromachined spiked biopotential electrodes," Biomedical Engineering, IEEE Transactions (Jun. 2002), 8 pages.

"User monitoring," Sapien Systems, available at http://web.archive.org/web/20030818043339/http:/www.sapiensystems.com/eyetracking.html, (Aug. 18, 2003), 1 page.

Klimesch, "EEG alpha and theta oscillations reflect cognitive and memory performanceJul. 20, 2012 a review and analysis," Brain Research Reviews, vol. 29, 169-195, (1999), 27 pages.

Second Office Action, issued by the State Intellectual Property Office of P.R. China in connection with Patent Application No. 200880104982.1, on Jun. 29, 2012, 5 pages.

Notice of Allowance, issued by the United States Patent and Trademark Office in connection with U.S. Appl. No. 12/357,302, on May 7, 2012, 16 pages.

Notice of Allowance, issued by the United States Patent and Trademark Office in connection with U.S. Appl. No. 12/868,531, on May 8, 2012, 16 pages.

Notice of Allowance, issued by the United States Patent and Trademark Office in connection with U.S. Appl. No. 12/608,696, on May 15, 2012, 16 pages.

Restriction Requirement, issued by the United States Patent and Trademark Office in connection with U.S. Appl. No. 12/545,455, on Jun. 13, 2012, 5 pages.

Office Action, issued by the United States Patent and Trademark Office in connection with U.S. Appl. No. 12/056,225, on Jun. 15, 2012, 9 pages.

Office Action, issued by the United States Patent and Trademark Office in connection with U.S. Appl. No. 12/544,934, on Jun. 18, 2012, 11 pages.

Office Action, issued by the United States Patent and Trademark Office in connection with U.S. Appl. No. 12/135,066, on Jun. 21, 2012, 9 pages.

Final Rejection, issued by the United States Patent and Trademark Office in connection with U.S. Appl. No. 12/608,660, on Jul. 10, 2012, 13 pages.

Second Office Action, issued by the State Intellectual Property Office of P.R. China in connection with Patent Application No. 200880019166.0, on Jun. 5, 2012, 8 pages.
Barreto et al., "Physiologic Instrumentation for Real-time Monitoring of Affective State of Computer Users," WSEAS International Conference on Instrumentation, Measurement, Control, Circuits and Systems (IMCCAS), (2004), 6 pages.
Jung et al., "Analysis and Visualization of Single-Trial Event-Related Potentials," Human Brain Mapping vol. 14, 166-185 (2001), 20 pages.
Krugman, "Brain Wave Measures of Media Involvement," Journal of Advertising Research vol. 11, 3-9 (Feb. 1971), 7 pages.
The Mathworks, Inc., "MATLAB Data Analysis: Version 7," p. 4-19 (2005), 3 pages.
Krakow et al., "Methodology: EEG-correlated fMRI," Functional Imaging in the Epilepsies, (Lippincott Williams & Wilkins, 2000), 17 pages.
Allen et al., "A Method of Removing Imaging Artifact from Continuous EEG Recorded during Functional MRI," Neuroimage, vol. 12, 230-239, (Aug. 2000).
Office Action, issued by the United States Patent and Trademark Office in connection with U.S. Appl. No. 12/544,921, on Jan. 9, 2012, 13 pages.
Office Action, issued by the United States Patent and Trademark Office in connection with U.S. Appl. No. 12/357,302, on Jan. 17, 2012, 11 pages.
Office Action, issued by the United States Patent and Trademark Office in connection with U.S. Appl. No. 12/056,225, on Jan. 20, 2012, 12 pages.
Final Rejection, issued by the United States Patent and Trademark Office in connection with U.S. Appl. No. 12/135,066, on Jan. 24, 2012, 12 pages.
Office Action, issued by the United States Patent and Trademark Office in connection with U.S. Appl. No. 12/546,586, on Feb. 1, 2012, 17 pages.
Restriction Requirement, issued by the United States Patent and Trademark Office in connection with U.S. Appl. No. 12/544,958, on Feb. 10, 2012, 6 pages.
Final Rejection, issued by the United States Patent and Trademark Office in connection with U.S. Appl. No. 12/135,069, on Feb. 14, 2012, 35 pages.
Final Rejection, issued by the United States Patent and Trademark Office in connection with U.S. Appl. No. 12/357,322, on Feb. 14, 2012, 14 pages.
Office Action, issued by the United States Patent and Trademark Office in connection with U.S. Appl. No. 12/056,211, on Feb. 16, 2012, 15 pages.
Final Rejection, issued by the United States Patent and Trademark Office in connection with U.S. Appl. No. 12/056,190, on Feb. 17, 2012, 22 pages.
Office Action, issued by the United States Patent and Trademark Office in connection with U.S. Appl. No. 12/122,253, on Feb. 17, 2012, 20 pages.
Office Action, issued by the United States Patent and Trademark Office in connection with U.S. Appl. No. 12/182,874, on Feb. 17, 2012, 15 pages.
First Office Action, issued by the State Intellectual Property Office of P.R. China in connection with Patent Application No. 200880017883.X, on Nov. 30, 2011, 16 pages.
Meriam-Webster Online Dictionary definition for "tangible," available at http://www.meriam-webster.com/dictionary/tangible, 1 page.
Mosby's Dictionary of Medicine, Nursing, & Health Professions, 2009, Mosby, Inc., Definition of Alpha Wave, 1 page.
Mosby's Dictionary of Medicine, Nursing, & Health Professions, 2009, Mosby, Inc., Definition of Beta Wave, 1 page.
U.S. Appl. No. 13/249,512, filed Sep. 30, 2011, (unpublished).
U.S. Appl. No. 13/249,525, filed Sep. 30, 2011, (unpublished).
U.S. Appl. No. 13/288,504, filed Nov. 3, 2011, (unpublished).
U.S. Appl. No. 13/288,571, filed Nov. 3, 2011, (unpublished).
U.S. Appl. No. 12/304,234, filed Nov. 3, 2011, (unpublished).
Examiner's Answer, issued by the United States Patent and Trademark Office in connection with U.S. Appl. No. 12/234,372, on May 23, 2012, 11 pages.
Advisory Action, issued by the United States Patent and Trademark Office in connection with U.S. Appl. No. 12/234,388, on Aug. 28, 2012, 3 pages.
Examiner's Answer, issued by the United States Patent and Trademark Office in connection with U.S. Appl. No. 12/410,380, on Jun. 8, 2012, 12 pages.
Examiner's Answer, issued by the United States Patent and Trademark Office in connection with U.S. Appl. No. 12/410,372, on Aug. 3, 2012, 8 pages.
Office Action, issued by the United States Patent and Trademark Office in connection with U.S. Appl. No. 12/545,455, on Aug. 29, 2012, 11 pages.
Final Rejection, issued by the United States Patent and Trademark Office in connection with U.S. Appl. No. 12/608,685, on Jul. 30, 2012, 15 pages.
Office Action, issued by the United States Patent and Trademark Office in connection with U.S. Appl. No. 12/778,810, on Aug. 31, 2012, 12 pages.
Office Action, issued by the United States Patent and Trademark Office in connection with U.S. Appl. No. 12/778,828, on Aug. 30, 2012, 9 pages.
Second Office Action, issued by the State Intellectual Property Office of China in connection with Chinese Patent Application No. 200880017883.X, on Aug. 10, 2012 (9 pages).
Oberman et al., "EEG evidence for mirror neuron activity during the observation of human and robot actions: Toward an analysis of the human qualities of interactive robots," Elsevier, Neurocomputing vol. 70 (2007), Jan. 2, 2007 (10 pages).
Notice of Allowance, issued by the United States Patent and Trademark Office in connection with U.S. Appl. No. 12/056,190, on Sep. 17, 2012, 11 pages.
Final Rejection, issued by the United States Patent and Trademark Office in connection with U.S. Appl. No. 12/122,253, on Sep. 17, 2012, 17 pages.
Examiner's Answer, issued by the United States Patent and Trademark Office in connection with U.S. Appl. No. 12/413,297, on Sep. 18, 2012, 18 pages.
Final Rejection, issued by the United States Patent and Trademark Office in connection with U.S. Appl. No. 12/546,586, on Sep. 18, 2012, 17 pages.
Notice of Allowance, issued by the United States Patent and Trademark Office in connection with U.S. Appl. No. 12/056,211, on Sep. 19, 2012, 10 pages.
Notice of Allowance, issued by the United States Patent and Trademark Office in connection with U.S. Appl. No. 12/135,074, on Sep. 19, 2012, 10 pages.
Notice of Allowance, issued by the United States Patent and Trademark Office in connection with U.S. Appl. No. 12/200,813, on Sep. 20, 2012, 11 pages.
Notice of Allowance, issued by the United States Patent and Trademark Office in connection with U.S. Appl. No. 12/853,213, on Sep. 7, 2012, 9 pages.
Notice of Allowance, issued by the United States Patent and Trademark Office in connection with U.S. Appl. No. 12/199,583, on Sep. 26, 2012, 14 pages.
Notice of Allowance, issued by the United States Patent and Trademark Office in connection with U.S. Appl. No. 12/199,596, on Sep. 27, 2012, 14 pages.
English Translation of Office Action, issued by the Israel Patent Office in connection with Patent Application No. 203176, on Sep. 27, 2012, 1 pages.
English Translation of Office Action, issued by the Israel Patent Office in connection with Patent Application No. 203177, on Sep. 27, 2012, 1 pages.
Notice of Allowance, issued by the United States Patent and Trademark Office in connection with U.S. Appl. No. 12/199,557, on Sep. 28, 2012, 12 pages.
Notice of Allowance, issued by the United States Patent and Trademark Office in connection with U.S. Appl. No. 12/113,863, on Oct. 1, 2012, 12 pages.
Office Action, issued by the United States Patent and Trademark Office in connection with U.S. Appl. No. 13/444,149, on Oct. 4, 2012, 9 pages.

Final Office Action, issued by the United States Patent and Trademark Office in connection with U.S. Appl. No. 12/182,851, on Oct. 4, 2012, 14 pages.
Office Action, issued by the United States Patent and Trademark Office in connection with U.S. Appl. No. 12/234,388, on Oct. 5, 2012, 6 pages.
Office Action, issued by the Japanese Patent Office in connection with Patent Application No. 2010-501190, on Oct. 5, 2012, 5 pages.
Notice of Allowance, issued by the United States Patent and Trademark Office in connection with U.S. Appl. No. 12/853,197, on Oct. 16, 2012, 5 pages.
Notice of Allowance, issued by the United States Patent and Trademark Office in connection with U.S. Appl. No. 12/868,531, on Oct. 22, 2012, 5 pages.
English Translation of Office Action, issued by the Japanese Patent Office in connection with Patent Application No. 2010-506646, on Oct. 23, 2012, 3 pages.
Final Office Action, issued by the United States Patent and Trademark Office in connection with U.S. Appl. No. 12/846,242, on Nov. 29, 2012, 14 pages.
Clemons, "Resonance Marketing in the Age of the Truly Informed Consumer: Creating Profits through Differentiation and Delight," Wharton Information Strategy & Economics Blog 2, available at http://opim.wharton.upenn.edu/~clemons/blogs/resonanceblog.pdf, (Mar. 28, 2007), 8 pages.
Notice of Allowance, issued by the United States Patent and Trademark Office in connection with U.S. Appl. No. 12/200,813, on Nov. 2, 2012, 5 pages.
Notice of Allowance, issued by the United States Patent and Trademark Office in connection with U.S. Appl. No. 12/056,190, on Nov. 2, 2012, 5 pages.
Restriction Requirement, issued by the United States Patent and Trademark Office in connection with U.S. Appl. No. 12/056,225, on Nov. 2, 2012, 5 pages.
Final Office Action, issued by the United States Patent and Trademark Office in connection with U.S. Appl. No. 12/135,066, on Nov. 13, 2012, 9 pages.
Notice of Allowance, issued by the United States Patent and Trademark Office in connection with U.S. Appl. No. 12/113,863, on Nov. 16, 2012, 5 pages.
Notice of Allowance, issued by the United States Patent and Trademark Office in connection with U.S. Appl. No. 12/056,211, on Nov. 21, 2012, 5 pages.
Notice of Allowance, issued by the United States Patent and Trademark Office in connection with U.S. Appl. No. 12/868,531, on Nov. 23, 2012, 5 pages.
Office Action, issued by the United States Patent and Trademark Office in connection with U.S. Appl. No. 12/913,102, on Dec. 7, 2012, 7 pages.
Final Office Action, issued by the United States Patent and Trademark Office in connection with U.S. Appl. No. 12/544,958, on Dec. 10, 2012, 16 pages.
Notice of Allowance, issued by the United States Patent and Trademark Office in connection with U.S. Appl. No. 12/056,190, on Dec. 20, 2012, 5 pages.
Notice of Allowance, issued by the United States Patent and Trademark Office in connection with U.S. Appl. No. 12/056,190, Dec. 21, 2012, 14 pages.
Notice of Allowance, issued by the United States Patent and Trademark Office in connection with U.S. Appl. No. 12/056,211, on Dec. 21, 2012, 10 pages.
Notice of Allowance, issued by the United States Patent and Trademark Office in connection with U.S. Appl. No. 12/135,074, on Dec. 21, 2012, 12 pages.
Notice of Allowance, issued by the United States Patent and Trademark Office in connection with U.S. Appl. No. 12/199,557, on Dec. 21, 2012, 14 pages.
Notice of Allowance, issued by the United States Patent and Trademark Office in connection with U.S. Appl. No. 12/199,596, on Dec. 21, 2012, 17 pages.
Notice of Allowance, issued by the United States Patent and Trademark Office in connection with U.S. Appl. No. 12/200,813, on Dec. 21, 2012, 9 pages.
Notice of Allowance, issued by the United States Patent and Trademark Office in connection with U.S. Appl. No. 12/853,213, on Dec. 21, 2012, 10 pages.
Notice of Allowance, issued by the United States Patent and Trademark Office in connection with U.S. Appl. No. 12/868,531, on Dec. 26, 2012, 2 pages.
Notice of Allowance, issued by the United States Patent and Trademark Office in connection with U.S. Appl. No. 12/113,863, on Dec. 31, 2012, 5 pages.
Notice of Allowance, issued by the United States Patent and Trademark Office in connection with U.S. Appl. No. 12/199,583, on Dec. 31, 2012, 10 pages.
Final Office Action, issued by the United States Patent and Trademark Office in connection with U.S. Appl. No. 12/182,874, on Jan. 4, 2013, 17 pages.
Notice of Allowance, issued by the United States Patent and Trademark Office in connection with U.S. Appl. No. 12/199,583, on Jan. 11, 2013, 11 pages.
Final Office Action, issued by the United States Patent and Trademark Office in connection with U.S. Appl. No. 12/056,225, on Jan. 11, 2013, 11 pages.
English Translation of Office Action, issued by the Israeli Patent Office in connection with Patent Application No. 201187, on Nov. 27, 2012, 2 pages.
English Translation of Third Office Action, issued by the State Intellectual Property Office of P.R. China in connection with Patent Application No. 200880101500.7, on Nov. 21, 2012, 5 pages.
Extended European Search Report, issued by the European Patent Office in connection with European Application No. 08796890.5-2319/2170161, on Dec. 7, 2012, 9 pages.
Palva et al., "Phase Synchrony Among Neuronal Oscillations in the Human Cortex," Journal of Neuroscience 25 (2005), 3962-3972, 11 pages.
Lachaux et al., "Measuring Phase Synchrony in Brain Signals," Human Brain Mapping 8 (1999), 194-208, 15 pages.

* cited by examiner

| Stimulus Attributes Data Model 201 | | | | | |
|---|---|---|---|---|---|
| Channel 203 | Media 205 | Time Span 207 | Audience 209 | Demography 211 | ... |

| Stimulus Purpose Data Model 215 | | |
|---|---|---|
| Intent 217 | Objectives 219 | ... |

Figure 2

Dataset Data Model 301

| Experiment Name 303 | Client Attributes 305 | Subject Pool 307 | Logistics Information 309 | Stimulus Material 311 | ... |

Subject Attributes Data Model 315

| Subject Name 317 | Demographic Attributes 319 | Contact Information 321 | ... |

Neuro-Feedback Association Data Model 325

| Experiment Protocols 327 | Modalities included 329 | Experiment Design Parameters 333 | ... |

Data Collection Data Model 337

| Recording Attributes 339 | Equipment Attributes 341 | Modalities Recorded 343 | Data Storage Attributes 345 | ... |

Preset Query Data Model 349

| Query Name 351 | Accessed Data Collection 353 | Access Security Attributes 355 | Refresh Attributes 357 |

Figure 3

| Subject Attributes Queries 415 | | |
|---|---|---|
| Location 417 | Demographic Attributes 419 | Session Information 421 | ... |

| Experimental Design Queries 425 | | |
|---|---|---|
| Experiment Protocols 427 | Product Category 429 | Surveys Included 431 | Stimulus Used 433 | ... |

| Response Assessment Queries 437 | | |
|---|---|---|
| Attention Score 439 | Emotion Score 441 | Retention Score 443 | Effectiveness Score 445 | ... |

Figure 4

| Client Assessment Summary Reports 501 | | |
|---|---|---|
| Effectiveness 503 | Component Assessment 505 | Audience Response 507 | ... |

| Client Cumulative Reports 511 | | |
|---|---|---|
| Media Grouped 513 | Campaign Grouped 515 | Time/Location Grouped 517 | ... |

| Industry Cumulative And Syndicated Reports 521 | | | | |
|---|---|---|---|---|
| Aggregate Assessment 523 | Top Performers 525 | Bottom Performers 527 | Outliers 529 | Trend 531 | ... |

Figure 5

NEURO-PHYSIOLOGY AND NEURO-BEHAVIORAL BASED STIMULUS TARGETING SYSTEM

CROSS REFERENCE TO RELATED APPLICATIONS

This patent claims priority to Provisional Patent Application 60/938,286 titled Neuro-Physiology And Neuro-Behavior Based Stimulus Targeting System, by Anantha Pradeep, Robert T. Knight, and Ramachandran Gurumoorthy, and filed on May 16, 2007. This patent is related to U.S. patent application Ser. Nos. 12/056,190; 12/056,211; 12/056,221; 12/056,225; 12/113,863; 12/113,870; 12/122,240; 12/122,253; 12/135,066; 12/135,074; 12/182,851; 12/182,874; 12/199,557; 12/199,583; 12/199,596; 12/200,813; 12/234,372; 12/135,069; 12/234,388; 12/544,921; 12/544,934; 12/546,586; 12/544,958; 12/846,242; 12/410,380; 12/410,372; 12/413,297; 12/545,455; 12/608,660; 12/608,685; 13/444,149; 12/608,696; 12/731,868; 13/045,457; 12/778,810; 12/778,828; 13/104,821; 13/104,840; 12/853,197; 12/884,034; 12/868,531; 12/913,102; 12/853,213; and 13/105,774.

TECHNICAL FIELD

The present disclosure relates to a neuro-physiology and neuro-behavior based stimulus target system.

DESCRIPTION OF RELATED ART

Conventional systems for selectively targeting stimulus materials such as advertising often rely on general geographic, demographic, or statistical information. In some instances, conventional system selectively target stimulus materials using survey based response collection. However, these mechanisms for selectively targeting stimulus materials are limited.

BRIEF DESCRIPTION OF THE DRAWINGS

The disclosure may best be understood by reference to the following description taken in conjunction with the accompanying drawings, which illustrate particular example embodiments.

FIG. 2 illustrates examples of stimulus attributes that can be included in a stimulus attributes repository.

FIG. 3 illustrates examples of data models that can be used with the stimulus targeting system.

FIG. 4 illustrates one example of a query that can be used with the stimulus targeting system.

FIG. 5 illustrates one example of a report generated using the stimulus targeting system.

DESCRIPTION OF PARTICULAR EMBODIMENTS

Figure 1:
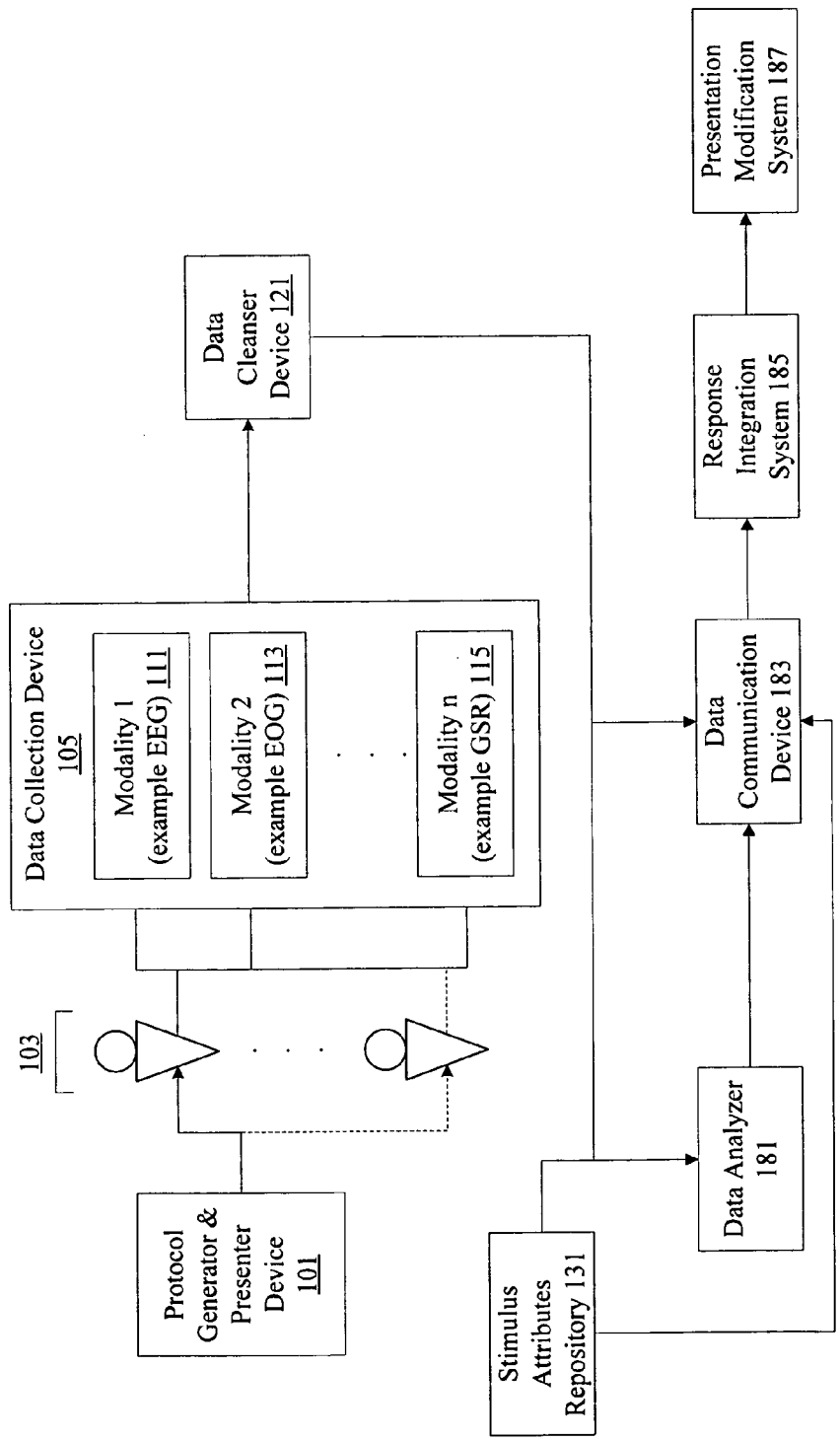
FIG. 1 illustrates one example of a system for performing stimulus targeting.

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

For example, the techniques and mechanisms of the present invention will be described in the context of particular types of neuro-physiological and neuro-behavioral data. However, it should be noted that the techniques and mechanisms of the present invention apply to a variety of different types of data. It should be noted that various mechanisms and techniques can be applied to any type of stimuli. In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise. For example, a system uses a processor in a variety of contexts. However, it will be appreciated that a system can use multiple processors while remaining within the scope of the present invention unless otherwise noted. Furthermore, the techniques and mechanisms of the present invention will sometimes describe a connection between two entities. It should be noted that a connection between two entities does not necessarily mean a direct, unimpeded connection, as a variety of other entities may reside between the two entities. For example, a processor may be connected to memory, but it will be appreciated that a variety of bridges and controllers may reside between the processor and memory. Consequently, a connection does not necessarily mean a direct, unimpeded connection unless otherwise noted.

Overview

It is desirable to provide improved methods and apparatus for providing a stimulus targeting system.

A system performs stimulus targeting using neuro-physiological and neuro-behavioral data. Subjects are exposed to stimulus material such as marketing and entertainment materials and data is collected using mechanisms such as Electroencephalography (EEG), Galvanic Skin Response (GSR), Electrocardiograms (EKG), Electrooculography (EOG), eye tracking, and facial emotion encoding. Neuro-physiological and neuro-behavioral data collected is analyzed to select targeted stimulus materials. The targeted stimulus materials are provided to particular subjects for a variety of purposes.

Example Embodiments

Conventional stimulus targeting systems typically target general geographic areas and demographic groups and do not have the resolution to target narrow audiences or individuals. Some efforts have been made to selectively target narrow audiences or individuals, but these efforts have been limited because of a variety of reasons.

For example, subjects are required to complete surveys after initial and subsequent exposures to stimulus material such as an advertisement. The survey responses are analyzed to determine possible patterns. However, survey results often provide only limited information. For example, survey subjects may be unable or unwilling to express their true thoughts and feelings about a topic, or questions may be phrased with built in bias. Articulate subjects may be given more weight than non-expressive ones. Analysis of multiple survey responses and correlation of the responses to stimulus material is also limited. A variety of semantic, syntactic, metaphorical, cultural, social and interpretive biases and errors prevent accurate and repeatable evaluation.

Consequently, the techniques and mechanisms of the present invention use neuro-physiological and neuro-behavioral response measurements such as central nervous system, autonomic nervous system, and effector measurements to improve stimulus targeting. Some examples of central nervous system measurement mechanisms include Functional Magnetic Resonance Imaging (fMRI) and Electroencephalography (EEG). fMRI measures blood oxygenation in the brain that correlates with increased neural activity. However, current implementations of fMRI have poor temporal resolution of few seconds. EEG measures electrical activity associated with post synaptic currents occurring in the milliseconds range. Subcranial EEG can measure electrical activity with the most accuracy, as the bone and dermal layers weaken transmission of a wide range of frequencies. Nonetheless, surface EEG provides a wealth of electrophysiological information if analyzed properly.

Autonomic nervous system measurement mechanisms include Galvanic Skin Response (GSR), Electrocardiograms (EKG), pupillary dilation, etc. Effector measurement mechanisms include Electrooculography (EOG), eye tracking, facial emotion encoding, reaction time etc.

According to various embodiments, the techniques and mechanisms of the present invention intelligently blend multiple modes and manifestations of precognitive neural signatures with cognitive neural signatures and post cognitive neurophysiological manifestations to more accurately allow selective targeting of stimulus materials. In some examples, autonomic nervous system measures are themselves used to validate central nervous system measures. Effector and behavior responses are blended and combined with other measures. According to various embodiments, central nervous system, autonomic nervous system, and effector system measurements are aggregated into a measurement that allows selective targeting of stimulus materials.

In particular embodiments, multiple subjects are exposed to stimulus material and data such as neuro-physiological and neuro-behavioral data. According to various embodiments, the multiple subjects may be exposed simultaneously to stimulus material in a large group setting, in multiple small group settings, in relatively isolated settings, etc. The multiple subjects may or may not be allowed to interact directly or indirectly. Response data collected during exposure of the multiple subjects is analyzed and integrated to determine neuro-physiological and neuro-behavioral response data. According to various embodiments, response data is analyzed and enhanced for each subject and further analyzed and enhanced by integrating data across multiple subjects to select stimulus materials to provide to particular subjects.

According to various embodiments, neuro-physiological and neuro-behavioral data may show particular effectiveness of stimulus material for a particular subset of individuals. In particular embodiments, neuro-physiological and neuro-behavioral data may show profiles of responses for particular subjects based on attributes of the stimulus material. Targeted stimulus materials may be intelligently selected using neuro-physiological and neuro-behavioral data and known attributes of the stimulus materials. In some examples, survey results and focus group information can also be used to elicit further insights on selecting stimulus materials. The additional stimulus materials selected may be used to obtain additional neuro-physiological and neuro-behavioral information from particular subjects. The additional stimulus materials may also be selected as materials that would be particularly effective in an advertising campaign or mailing campaign. Stimulus materials may be targeted to narrow audiences, individuals, or even specific subgroups or larger populations.

A variety of stimulus materials such as entertainment and marketing materials, media streams, billboards, print advertisements, text streams, music, performances, sensory experiences, etc. can be analyzed. According to various embodiments, enhanced neuro-physiological and neuro-behavioral data is generated using a data analyzer that performs both intra-modality measurement enhancements and cross-modality measurement enhancements. According to various embodiments, brain activity is measured not just to determine the regions of activity, but to determine interactions and types of interactions between various regions. The techniques and mechanisms of the present invention recognize that interactions between neural regions support orchestrated and organized behavior. Attention, emotion, memory, and other abilities are not merely based on one part of the brain but instead rely on network interactions between brain regions.

The techniques and mechanisms of the present invention further recognize that different frequency bands used for multi-regional communication can be indicative of the effectiveness of stimuli. In particular embodiments, evaluations are calibrated to each subject and synchronized across subjects. In particular embodiments, templates are created for subjects to create a baseline for measuring pre and post stimulus differentials. According to various embodiments, stimulus generators are intelligent and adaptively modify specific parameters such as exposure length and duration for each subject being analyzed. An intelligent stimulus generation mechanism intelligently adapts output for particular users and purposes. A variety of modalities can be used including EEG, GSR, EKG, pupillary dilation, EOG, eye tracking, facial emotion encoding, reaction time, etc. Individual modalities such as EEG are enhanced by intelligently recognizing neural region communication pathways.

Cross modality analysis is enhanced using a synthesis and analytical blending of central nervous system, autonomic nervous system, and effector signatures. Synthesis and analysis by mechanisms such as time and phase shifting, correlating, and validating intra-modal determinations allow generation of a composite output characterizing the significance of various data responses. Responses can be integrated across subjects and additional stimulus material can be targeted to particular subjects and groups using responses and stimulus material attributes.

FIG. 1 illustrates one example of a system for performing stimulus targeting using central nervous system, autonomic nervous system, and effector measures. According to various embodiments, the stimulus targeting system includes a protocol generator and presenter device 101. In particular embodiments, the protocol generator and presenter device 101 is merely a presenter device and merely presents stimulus material to a user. The stimulus material may be a media clip, a commercial, pages of text, a brand image, a performance, a magazine advertisement, a movie, an audio presentation, particular tastes, smells, textures and/or sounds. The stimuli can involve a variety of senses and occur with or without human supervision. Continuous and discrete modes are supported. According to various embodiments, the protocol generator and presenter device 101 also has protocol generation capability to allow intelligent customization of stimuli provided to multiple subjects.

According to various embodiments, the subjects are connected to data collection devices 105. The data collection devices 105 may include a variety of neuro-physiological and neuro-behavioral measurement mechanisms such as EEG, EOG, GSR, EKG, pupillary dilation, eye tracking, facial emotion encoding, and reaction time devices, etc. According to various embodiments, neuro-physiological and neuro-behavioral data includes central nervous system, autonomic nervous system, and effector data. In particular embodiments, the data collection devices 105 include EEG 111, EOG 113, and GSR 115. In some instances, only a single data collection device is used. Data collection may proceed with or without human supervision.

The data collection device 105 collects neuro-physiological and neuro-behavioral data from multiple sources. This includes a combination of devices such as central nervous system sources (EEG), autonomic nervous system sources (GSR, EKG, pupillary dilation), and effector sources (EOG, eye tracking, facial emotion encoding, reaction time). In particular embodiments, data collected is digitally sampled and stored for later analysis. In particular embodiments, the data collected could be analyzed in real-time. According to particular embodiments, the digital sampling rates are adaptively chosen based on the neurophysiological and neurological data being measured.

In one particular embodiment, the stimulus targeting system includes EEG 111 measurements made using scalp level electrodes, EOG 113 measurements made using shielded electrodes to track eye data, GSR 115 measurements performed using a differential measurement system, a facial muscular measurement through shielded electrodes placed at specific locations on the face, and a facial affect graphic and video analyzer adaptively derived for each individual.

In particular embodiments, the data collection devices are clock synchronized with a protocol generator and presenter device 101. The data collection system 105 can collect data from individual subjects (1 system), or can be modified to collect synchronized data from multiple subjects (N+1 system). The N+1 system may include multiple individuals synchronously tested in isolation or in a group setting. In particular embodiments, the subjects are placed in a large group setting and are allowed to interact while being exposed to the stimulus material. In other examples, subjects are placed in a group setting but are allowed only non-verbal interaction. In still other examples, subjects are not allowed to interact during exposure to stimulus materials. A variety of arrangements are possible. In particular embodiments, the data collection devices also include a condition evaluation subsystem that provides auto triggers, alerts and status monitoring and visualization components that continuously monitor the status of the subject, data being collected, and the data collection instruments. The condition evaluation subsystem may also present visual alerts and automatically trigger remedial actions.

According to various embodiments, the stimulus targeting system also includes a data cleanser device 121. In particular embodiments, the data cleanser device 121 filters the collected data to remove noise, artifacts, and other irrelevant data using fixed and adaptive filtering, weighted averaging, advanced component extraction (like PCA, ICA), vector and component separation methods, etc. This device cleanses the data by removing both exogenous noise (where the source is outside the physiology of the subject) and endogenous artifacts (where the source could be neurophysiological like muscle movement, eye blinks, etc.).

The artifact removal subsystem includes mechanisms to selectively isolate and review the response data and identify epochs with time domain and/or frequency domain attributes that correspond to artifacts such as line frequency, eye blinks, and muscle movements. The artifact removal subsystem then cleanses the artifacts by either omitting these epochs, or by replacing these epoch data with an estimate based on the other clean data (for example, an EEG nearest neighbor weighted averaging approach).

According to various embodiments, the data cleanser device 121 is implemented using hardware, firmware, and/or software. It should be noted that although a data cleanser device 121 is shown located after a data collection device 105 and before data analyzer 181, the data cleanser device 121 like other components may have a location and functionality that varies based on system implementation. For example, some systems may not use any automated data cleanser device whatsoever while in other systems, data cleanser devices may be integrated into individual data collection devices.

A stimulus attributes repository 131 provides information on the stimulus material being presented to the multiple subjects. According to various embodiments, stimulus attributes include properties of the stimulus materials as well as purposes, presentation attributes, report generation attributes, etc. In particular embodiments, stimulus attributes include time span, channel, rating, media, type, etc. Purpose attributes include aspiration and objects of the stimulus including excitement, memory retention, associations, etc. Presentation attributes include audio, video, imagery, and message needed for enhancement or avoidance. Other attributes may or may not also be included in the stimulus attributes repository or some other repository.

The data cleanser device 121 and the stimulus attributes repository 131 pass data to the data analyzer 181. The data analyzer 181 uses a variety of mechanisms to analyze underlying data in the system to determine neuro-physiological and neuro-behavioral characteristics of stimulus material. According to various embodiments, the data analyzer customizes and extracts the independent neurological and neuro-physiological parameters for each individual in each modality, and blends the estimates within a modality as well as across modalities to elicit an enhanced response to the presented stimulus material. In particular embodiments, the data analyzer 181 aggregates the response measures across subjects in a dataset.

According to various embodiments, neuro-physiological and neuro-behavioral signatures are measured using time domain analyses and frequency domain analyses. Such analyses use parameters that are common across individuals as well as parameters that are unique to each individual. The analyses could also include statistical parameter extraction and fuzzy logic based attribute estimation from both the time and frequency components of the synthesized response.

In some examples, statistical parameters used in a blended effectiveness estimate include evaluations of skew, peaks, first and second moments, population distribution, as well as fuzzy estimates of attention, emotional engagement and memory retention responses.

According to various embodiments, the data analyzer 181 may include an intra-modality response synthesizer and a cross-modality response synthesizer. In particular embodiments, the intra-modality response synthesizer is configured to customize and extract the independent neuro-physiological and neuro-behavioral parameters for each individual in each modality and blend the estimates within a modality analytically to elicit an enhanced response to the presented stimuli.

In particular embodiments, the intra-modality response synthesizer also aggregates data from different subjects in a dataset.

According to various embodiments, the cross-modality response synthesizer or fusion device blends different intra-modality responses, including raw signals and signals output. The combination of signals enhances the measures of effectiveness within a modality. The cross-modality response fusion device can also aggregate data from different subjects in a dataset.

According to various embodiments, the data analyzer 181 also includes a composite enhanced effectiveness estimator (CEEE) that combines the enhanced responses and estimates from each modality to provide a blended estimate of the effectiveness. In particular embodiments, blended estimates are provided for each exposure of a subject to stimulus materials. The blended estimates are evaluated over time to determine neuro-physiological and neuro-behavioral characteristics. According to various embodiments, numerical values are assigned to each blended estimate. The numerical values may correspond to the intensity of neuro-physiological and neuro-behavioral measurements, the significance of peaks, the change between peaks, etc. Higher numerical values may correspond to higher significance in neuro-physiological and neuro-behavioral intensity. Lower numerical values may correspond to lower significance or even insignificance neuro-physiological and neuro-behavioral activity. In other examples, multiple values are assigned to each blended estimate. In still other examples, blended estimates of neuro-physiological and neuro-behavioral significance are graphically represented to show effectiveness for different individuals or groups.

According to various embodiments, the data analyzer 181 provides analyzed and enhanced response data to a data communication system 183. According to various embodiments, the data communication system 183 provides raw and/or analyzed data and insights to the response integration system. In particular embodiments, the data communication system 183 may include mechanisms for the compression and encryption of data for secure storage and communication.

According to various embodiments, the data communication system 183 transmits data to the response integration using protocols such as the File Transfer Protocol (FTP), Hypertext Transfer Protocol (HTTP) along with a variety of conventional, bus, wired network, wireless network, satellite, and proprietary communication protocols. The data transmitted can include the data in its entirety, excerpts of data, converted data, and/or elicited response measures.

In particular embodiments, the data communication system 183 sends data to response integration system 185. According to various embodiments, the response integration system 185 combines analyzed and enhanced responses to the stimulus material while using information about stimulus material attributes. In particular embodiments, the response integration system 185 also collects and integrates user behavioral and survey responses with the analyzed and enhanced response data to more effectively determine neuro-physiological and neuro-behavioral response to stimulus materials.

According to various embodiments, the response integration system 185 obtains attributes such as requirements and purposes of the stimulus material presented. Some of these requirements and purposes may be obtained from a stimulus attribute repository 131. Others may be obtained from other sources. In particular embodiments, the requirements collected include attributes of the stimulus material including channel, media, time span, audience, demographic target.

Other purposes may involve the target objectives of the stimulus material, such as memory retention of a brand name, association of a product with a particular feeling, etc. Still other attributes may include views and presentation specific attributes such as audio, video, imagery and messages needed, media for enhanced, media for avoidance, etc.

According to various embodiments, the response integration system 185 also includes mechanisms for the collection and storage of demographic, statistical and/or survey based responses to different entertainment, marketing, advertising and other audio/visual/tactile/olfactory material. If this information is stored externally, the response integration system 185 can include a mechanism for the push and/or pull integration of the data, such as querying, extraction, recording, modification, and/or updating.

According to various embodiments, the response integration system 185 integrates the requirements for the presented material, the assessed neuro-physiological and neuro-behavioral response measures, and the additional stimulus attributes such as demographic/statistical/survey based responses into a synthesized measure for the neuro-physiological and neuro-behavioral response to the stimuli for the selection of targeted stimulus material for presentation to particular individuals or groups.

The response integration system 185 can further include an adaptive learning component that refines user or group profiles and tracks variations in the neuro-physiological and neuro-behavioral response to particular stimuli or series of stimuli over time. This information can be made available for other purposes, such as use of the information for presentation attribute decision making. According to various embodiments, the response integration system 185 integrates analyzed responses to stimuli and uses stimuli attributes to generate information for the selection of selectively targeted additional stimulus material.

As with a variety of the components in the stimulus targeting system, the response integration system 185 and the presentation modification system 187 can be co-located with the rest of the system and the user, or could be implemented in a remote location. It could also be optionally separated into an assessment repository system that could be centralized or distributed at the provider or providers of the stimulus material. In other examples, the response integration system is housed at the facilities of a third party service provider accessible by stimulus material providers and/or users.

According to various embodiments, the presentation modification system 187 also includes mechanisms for modification of the presentation of stimulus materials in a manner appropriate for different presentation devices. For example, the presentation modification system 187 can include an automated channel selection device that can be controlled based on the outputs of the response integration system. In other examples, the presentation modification system 187 can include software/hardware calls into an electronic game or gaming consoles for modifying levels and choices in the game. In still other examples, the presentation modification system 187 can modify the actual images and messages displayed in entertainment materials based on data from the response integration system 185.

In particular embodiments, the presentation modification system 187 modifies portions of a video stream such as a billboard displayed in images in the video stream in order to customize messages or images shown on the billboard. A billboard in a video stream may default to a particular advertisement but may be modified to target a particular subject or group of subjects. Messages, audio sequences, and/or any other type of stimulus material may be modified or adjusted to selectively target stimulus material. In other examples, a product in an image can be dynamically modified to show different brand names based on neuro-physiological and neuro-behavioral responses.

FIG. 2 illustrates examples of data models that may be provided with a stimulus attributes repository. According to various embodiments, a stimulus attributes data model 201 includes a channel 203, media type 205, time span 207, audience 209, and demographic information 211. A stimulus purpose data model 215 may include intents 217 and objectives 219.

According to various embodiments, intents and objectives may include memory retention of a brand name, association of a product with a particular feeling, excitement level for a particular service, etc. The attributes may be useful in providing targeted stimulus materials to multiple subjects and tracking and evaluating the effectiveness of the stimulus materials.

FIG. 3 illustrates examples of data models that can be used for storage of information associated with tracking and measurement of neuro-physiological and neuro-behavioral response. According to various embodiments, a dataset data model 301 includes an experiment name 303 and/or identifier, client attributes 305, a subject pool 307, logistics information 309 such as the location, date, and time of testing, and stimulus material 311 including stimulus material attributes.

In particular embodiments, a subject attribute data model 315 includes a subject name 317 and/or identifier, contact information 321, and demographic attributes 319 that may be useful for review of neurological and neuro-physiological data. Some examples of pertinent demographic attributes include marriage status, employment status, occupation, household income, household size and composition, ethnicity, geographic location, sex, race. Other fields that may be included in data model 315 include shopping preferences, entertainment preferences, and financial preferences. Shopping preferences include favorite stores, shopping frequency, categories shopped, favorite brands. Entertainment preferences include network/cable/satellite access capabilities, favorite shows, favorite genres, and favorite actors. Financial preferences include favorite insurance companies, preferred investment practices, banking preferences, and favorite online financial instruments. A variety of subject attributes may be included in a subject attributes data model 315 and data models may be preset or custom generated to suit particular purposes.

According to various embodiments, data models for neuro-feedback association 325 identify experimental protocols 327, modalities included 329 such as EEG, EOG, GSR, surveys conducted, and experiment design parameters 333 such as segments and segment attributes. Other fields may include experiment presentation scripts, segment length, segment details like stimulus material used, inter-subject variations, intra-subject variations, instructions, presentation order, survey questions used, etc. Other data models may include a data collection data model 337. According to various embodiments, the data collection data model 337 includes recording attributes 339 such as station and location identifiers, the data and time of recording, and operator details. In particular embodiments, equipment attributes 341 include an amplifier identifier and a sensor identifier.

Modalities recorded 343 may include modality specific attributes like EEG cap layout, active channels, sampling frequency, and filters used. EOG specific attributes include the number and type of sensors used, location of sensors applied, etc. Eye tracking specific attributes include the type of tracker used, data recording frequency, data being recorded, recording format, etc. According to various embodiments, data storage attributes 345 include file storage conventions (format, naming convention, dating convention), storage location, archival attributes, expiry attributes, etc.

A preset query data model 349 includes a query name 351 and/or identifier, an accessed data collection 353 such as data segments involved (models, databases/cubes, tables, etc.), access security attributes 355 included who has what type of access, and refresh attributes 357 such as the expiry of the query, refresh frequency, etc. Other fields such as push-pull preferences can also be included to identify an auto push reporting driver or a user driven report retrieval system.

FIG. 4 illustrates examples of queries that can be performed to obtain data associated with stimulus targeting. According to various embodiments, queries are defined from general or customized scripting languages and constructs, visual mechanisms, a library of preset queries, diagnostic querying including drill-down diagnostics, and eliciting what if scenarios. According to various embodiments, subject attributes queries 415 may be configured to obtain data from a neuro-informatics repository using a location 417 or geographic information, session information 421 such as testing times and dates, and demographic attributes 419. Demographics attributes include household income, household size and status, education level, age of kids, etc.

Other queries may retrieve stimulus material based on shopping preferences of subject participants, countenance, physiological assessment, completion status. For example, a user may query for data associated with product categories, products shopped, shops frequented, subject eye correction status, color blindness, subject state, signal strength of measured responses, alpha frequency band ringers, muscle movement assessments, segments completed, etc. Experimental design based queries may obtain data from a neuro-informatics repository based on experiment protocols 427, product category 429, surveys included 431, and stimulus provided 433. Other fields that may used include the number of protocol repetitions used, combination of protocols used, and usage configuration of surveys.

Client and industry based queries may obtain data based on the types of industries included in testing, specific categories tested, client companies involved, and brands being tested. Response assessment based queries 437 may include attention scores 439, emotion scores, 441, retention scores 443, and effectiveness scores 445. Such queries may obtain materials that elicited particular scores.

Response measure profile based queries may use mean measure thresholds, variance measures, number of peaks detected, etc. Group response queries may include group statistics like mean, variance, kurtosis, p-value, etc., group size, and outlier assessment measures. Still other queries may involve testing attributes like test location, time period, test repetition count, test station, and test operator fields. A variety of types and combinations of types of queries can be used to efficiently extract data.

FIG. 5 illustrates examples of reports that can be generated. According to various embodiments, client assessment summary reports 501 include effectiveness measures 503, component assessment measures 505, and neuro-physiological and neuro-behavioral measures 507. Effectiveness assessment measures include composite assessment measure(s), industry/category/client specific placement (percentile, ranking, . . . ), actionable grouping assessment such as removing material, modifying segments, or fine tuning specific elements, etc, and the evolution of the effectiveness profile over time. In particular embodiments, component assessment reports include component assessment measures like attention, emotional engagement scores, percentile placement, ranking, etc. Component profile measures include time based evolution of the component measures and profile statistical assessments. According to various embodiments, reports include the number of times material is assessed, attributes of the multiple presentations used, evolution of the response assessment measures over the multiple presentations, and usage recommendations.

According to various embodiments, client cumulative reports 511 include media grouped reporting 513 of all stimulus assessed, campaign grouped reporting 515 of stimulus assessed, and time/location grouped reporting 517 of stimulus assessed. According to various embodiments, industry cumulative and syndicated reports 521 include aggregate assessment responses measures 523, top performer lists 525, bottom performer lists 527, outliers 529, and trend reporting 531. In particular embodiments, tracking and reporting includes specific products, categories, companies, brands.

Figure 6:
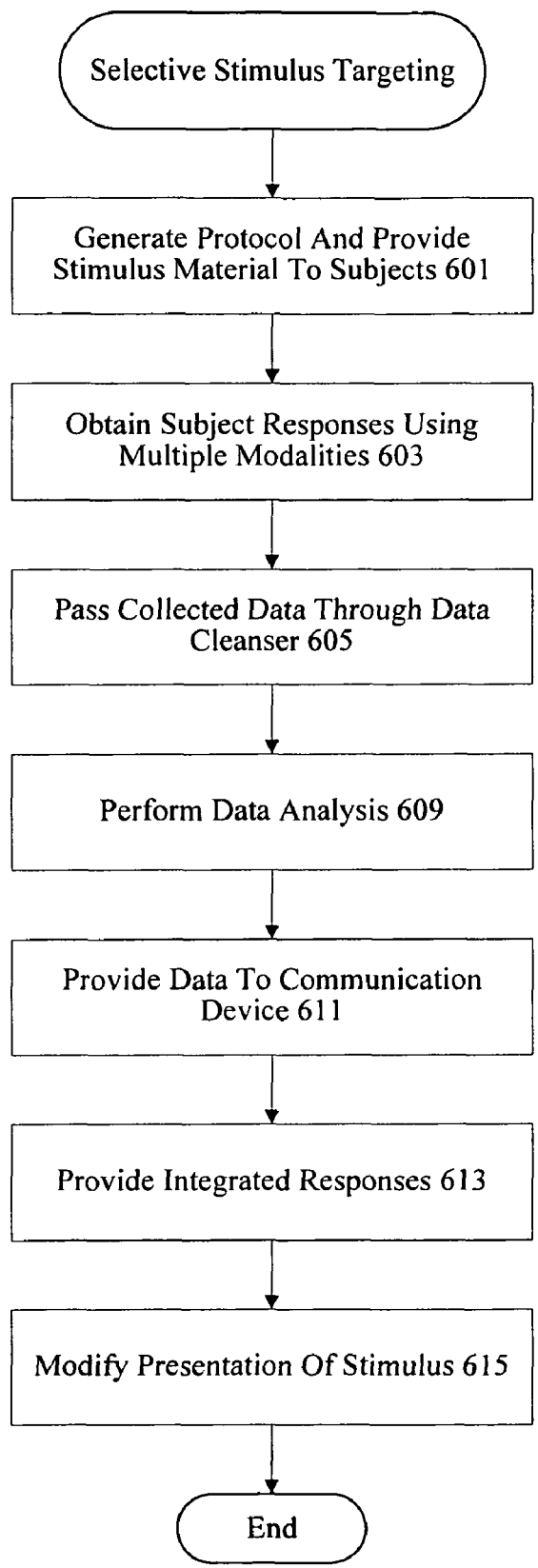
FIG. 6 illustrates one example of a technique for performing stimulus targeting.

FIG. 6 illustrates one example of stimulus targeting. At 601, a protocol is generated and stimulus material is provided to one or more subjects. According to various embodiments, stimulus includes streaming video, media clips, printed materials, presentations, performances, games, etc. The protocol determines the parameters surrounding the presentation of stimulus, such as the number of times shown, the duration of the exposure, sequence of exposure, segments of the stimulus to be shown, etc. Subjects may be isolated during exposure or may be presented materials in a group environment with or without supervision. At 603, subject responses are collected using a variety of modalities, such as EEG, ERP, EOG, GSR, etc. In some examples, verbal and written responses can also be collected and correlated with neurological and neurophysiological responses. At 605, data is passed through a data cleanser to remove noise and artifacts that may make data more difficult to interpret. According to various embodiments, the data cleanser removes EEG electrical activity associated with blinking and other endogenous/exogenous artifacts.

At 609, data analysis is performed. Data analysis may include intra-modality response synthesis and cross-modality response synthesis to enhance effectiveness measures. It should be noted that in some particular instances, one type of synthesis may be performed without performing other types of synthesis. For example, cross-modality response synthesis may be performed with or without intra-modality synthesis.

A variety of mechanisms can be used to perform data analysis 609. In particular embodiments, a stimulus attributes repository 131 is accessed to obtain attributes and characteristics of the stimulus materials, along with purposes, intents, objectives, etc. In particular embodiments, EEG response data is synthesized to provide an enhanced assessment of effectiveness. According to various embodiments, EEG measures electrical activity resulting from thousands of simultaneous neural processes associated with different portions of the brain. EEG data can be classified in various bands. According to various embodiments, brainwave frequencies include delta, theta, alpha, beta, and gamma frequency ranges. Delta waves are classified as those less than 4 Hz and are prominent during deep sleep. Theta waves have frequencies between 3.5 to 7.5 Hz and are associated with memories, attention, emotions, and sensations. Theta waves are typically prominent during states of internal focus.

Alpha frequencies reside between 7.5 and 13 Hz and typically peak around 10 Hz. Alpha waves are prominent during states of relaxation. Beta waves have a frequency range between 14 and 30 Hz. Beta waves are prominent during states of motor control, long range synchronization between brain areas, analytical problem solving, judgment, and decision making. Gamma waves occur between 30 and 60 Hz and are involved in binding of different populations of neurons together into a network for the purpose of carrying out a certain cognitive or motor function, as well as in attention and memory. Because the skull and dermal layers attenuate waves in this frequency range, brain waves above 75-80 Hz are difficult to detect and are often not used for stimuli response assessment.

However, the techniques and mechanisms of the present invention recognize that analyzing high gamma band (kappa-band: Above 60 Hz) measurements, in addition to theta, alpha, beta, and low gamma band measurements, enhances neurological attention, emotional engagement and retention component estimates. In particular embodiments, EEG measurements including difficult to detect high gamma or kappa band measurements are obtained, enhanced, and evaluated. Subject and task specific signature sub-bands in the theta, alpha, beta, gamma and kappa bands are identified to provide enhanced response estimates. According to various embodiments, high gamma waves (kappa-band) above 80 Hz (typically detectable with sub-cranial EEG and/or magnetoencephalograophy) can be used in inverse model-based enhancement of the frequency responses to the stimuli.

Various embodiments of the present invention recognize that particular sub-bands within each frequency range have particular prominence during certain activities. A subset of the frequencies in a particular band is referred to herein as a sub-band. For example, a sub-band may include the 40-45 Hz range within the gamma band. In particular embodiments, multiple sub-bands within the different bands are selected while remaining frequencies are band pass filtered. In particular embodiments, multiple sub-band responses may be enhanced, while the remaining frequency responses may be attenuated.

An information theory based band-weighting model is used for adaptive extraction of selective dataset specific, subject specific, task specific bands to enhance the effectiveness measure. Adaptive extraction may be performed using fuzzy scaling. Stimuli can be presented and enhanced measurements determined multiple times to determine the variation profiles across multiple presentations. Determining various profiles provides an enhanced assessment of the primary responses as well as the longevity (wear-out) of the marketing and entertainment stimuli. The synchronous response of multiple individuals to stimuli presented in concert is measured to determine an enhanced across subject synchrony measure of effectiveness. According to various embodiments, the synchronous response may be determined for multiple subjects residing in separate locations or for multiple subjects residing in the same location.

Although a variety of synthesis mechanisms are described, it should be recognized that any number of mechanisms can be applied—in sequence or in parallel with or without interaction between the mechanisms.

Although intra-modality synthesis mechanisms provide enhanced significance data, additional cross-modality synthesis mechanisms can also be applied. A variety of mechanisms such as EEG, Eye Tracking, GSR, EOG, and facial emotion encoding are connected to a cross-modality synthesis mechanism. Other mechanisms as well as variations and enhancements on existing mechanisms may also be included. According to various embodiments, data from a specific modality can be enhanced using data from one or more other modalities. In particular embodiments, EEG typically makes frequency measurements in different bands like alpha, beta and gamma to provide estimates of significance. However, the techniques of the present invention recognize that significance measures can be enhanced further using information from other modalities.

For example, facial emotion encoding measures can be used to enhance the valence of the EEG emotional engagement measure. EOG and eye tracking saccadic measures of object entities can be used to enhance the EEG estimates of significance including but not limited to attention, emotional engagement, and memory retention. According to various embodiments, a cross-modality synthesis mechanism performs time and phase shifting of data to allow data from different modalities to align. In some examples, it is recognized that an EEG response will often occur hundreds of milliseconds before a facial emotion measurement changes. Correlations can be drawn and time and phase shifts made on an individual as well as a group basis. In other examples, saccadic eye movements may be determined as occurring before and after particular EEG responses. According to various embodiments, time corrected GSR measures are used to scale and enhance the EEG estimates of significance including attention, emotional engagement and memory retention measures.

Evidence of the occurrence or non-occurrence of specific time domain difference event-related potential components (like the DERP) in specific regions correlates with subject responsiveness to specific stimulus. According to various embodiments, ERP measures are enhanced using EEG time-frequency measures (ERPSP) in response to the presentation of the marketing and entertainment stimuli. Specific portions are extracted and isolated to identify ERP, DERP and ERPSP analyses to perform. In particular embodiments, an EEG frequency estimation of attention, emotion and memory retention (ERPSP) is used as a co-factor in enhancing the ERP, DERP and time-domain response analysis.

EOG measures saccades to determine the presence of attention to specific objects of stimulus. Eye tracking measures the subject's gaze path, location and dwell on specific objects of stimulus. According to various embodiments, EOG and eye tracking is enhanced by measuring the presence of lambda waves (a neurophysiological index of saccade effectiveness) in the ongoing EEG in the occipital and extra striate regions, triggered by the slope of saccade-onset to estimate the significance of the EOG and eye tracking measures. In particular embodiments, specific EEG signatures of activity such as slow potential shifts and measures of coherence in time-frequency responses at the Frontal Eye Field (FEF) regions that preceded saccade-onset are measured to enhance the effectiveness of the saccadic activity data.

GSR typically measures the change in general arousal in response to stimulus presented. According to various embodiments, GSR is enhanced by correlating EEG/ERP responses and the GSR measurement to get an enhanced estimate of subject engagement. The GSR latency baselines are used in constructing a time-corrected GSR response to the stimulus. The time-corrected GSR response is co-factored with the EEG measures to enhance GSR significance measures.

According to various embodiments, facial emotion encoding uses templates generated by measuring facial muscle positions and movements of individuals expressing various emotions prior to the testing session. These individual specific facial emotion encoding templates are matched with the individual responses to identify subject emotional response. In particular embodiments, these facial emotion encoding measurements are enhanced by evaluating inter-hemispherical asymmetries in EEG responses in specific frequency bands and measuring frequency band interactions. The techniques of the present invention recognize that not only are particular frequency bands significant in EEG responses, but particular frequency bands used for communication between particular areas of the brain are significant. Consequently, these EEG responses enhance the EMG, graphic and video based facial emotion identification.

At 611, processed data is provided to a data communication device. Integrated responses are generated at 613. According to various embodiments, the data communication system data to the response integration using protocols such as the File Transfer Protocol (FTP), Hypertext Transfer Protocol (HTTP) along with a variety of conventional, bus, wired network, wireless network, satellite, and proprietary communication protocols. The data transmitted can include the data in its entirety, excerpts of data, converted data, and/or elicited response measures.

In particular embodiments, the data communication system sends data to the response integration system. According to various embodiments, the response integration system combines analyzed and enhanced responses to the stimulus material while using information about stimulus material attributes. In particular embodiments, the response integration system also collects and integrates user behavioral and survey responses with the analyzed and enhanced response data to more effectively measure and track neuro-physiological and neuro-behavioral response to stimulus materials. According to various embodiments, the response integration system obtains attributes such as requirements and purposes of the stimulus material presented.

Some of these requirements and purposes may be obtained from a variety of databases. According to various embodiments, the response integration system also includes mechanisms for the collection and storage of demographic, statistical and/or survey based responses to different entertainment, marketing, advertising and other audio/visual/tactile/olfactory material. If this information is stored externally, the response integration system can include a mechanism for the push and/or pull integration of the data, such as querying, extraction, recording, modification, and/or updating.

The response integration system can further include an adaptive learning component that refines user or group profiles and tracks variations in the neuro-physiological and neuro-behavioral response to particular stimuli or series of stimuli over time. This information can be made available for other purposes, such as use of the information for presentation attribute decision making. According to various embodiments, the response integration system builds and uses responses of users having similar profiles and demographics to provide integrated responses at 613. At 615, presentation of stimulus is modified to allow selective targeting of stimulus materials. According to various embodiments, additional stimulus materials for presentation to a particular subject or group of subjects are automatically selected based on integrated responses. In particular embodiments, a channel is automatically changed.

According to various embodiments, the targeted stimulus material is selected to elicit an as effective or more effective integrated response from the subject than the stimulus material originally presented to the subject. According to various embodiments, additional stimulus material is selected based on attribute similarities with the original stimulus material. In particular embodiments, various neurological and neuro-physiological measurements and combinations including attention, emotion, and memory retention are used to determine the significance of neuro-physiological and neuro-behavioral responses.

Figure 7:
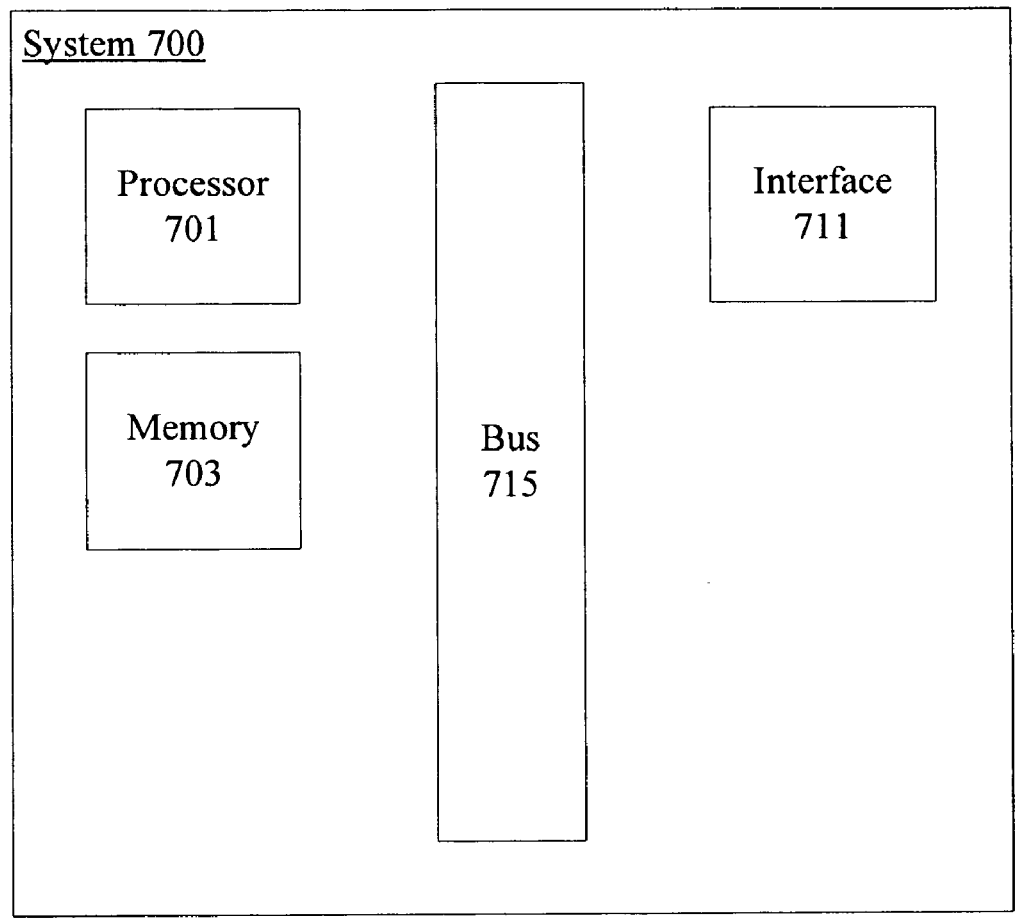
FIG. 7 provides one example of a system that can be used to implement one or more mechanisms.

According to various embodiments, various mechanisms such as the data collection mechanisms, the intra-modality synthesis mechanisms, cross-modality synthesis mechanisms, etc. are implemented on multiple devices. However, it is also possible that the various mechanisms be implemented in hardware, firmware, and/or software in a single system. FIG. 7 provides one example of a system that can be used to implement one or more mechanisms. For example, the system shown in FIG. 7 may be used to implement a data analyzer.

According to particular example embodiments, a system 700 suitable for implementing particular embodiments of the present invention includes a processor 701, a memory 703, an interface 711, and a bus 715 (e.g., a PCI bus). When acting under the control of appropriate software or firmware, the processor 701 is responsible for such tasks such as pattern generation. Various specially configured devices can also be used in place of a processor 701 or in addition to processor 701. The complete implementation can also be done in custom hardware. The interface 711 is typically configured to send and receive data packets or data segments over a network. Particular examples of interfaces the device supports include host bus adapter (HBA) interfaces, Ethernet interfaces, frame relay interfaces, cable interfaces, DSL interfaces, token ring interfaces, and the like.

In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as data synthesis.

According to particular example embodiments, the system 700 uses memory 703 to store data, algorithms and program instructions. The program instructions may control the operation of an operating system and/or one or more applications, for example. The memory or memories may also be configured to store received data and process received data.

Because such information and program instructions may be employed to implement the systems/methods described herein, the present invention relates to tangible, machine readable media that include program instructions, state information, etc. for performing various operations described herein. Examples of machine-readable media include, but are not limited to, magnetic media such as hard disks, floppy disks, and magnetic tape; optical media such as CD-ROM disks and DVDs; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Although the foregoing invention has been described in some detail for purposes of clarity of understanding, it will be apparent that certain changes and modifications may be practiced within the scope of the appended claims. Therefore, the present embodiments are to be considered as illustrative and not restrictive and the invention is not to be limited to the details given herein, but may be modified within the scope and equivalents of the appended claims.

What is claimed is:

1. A system, comprising:
a data collector to obtain first neuro-response data from a first frequency band measured in a first hemisphere and second neuro-response data from a second frequency band measured in a second hemisphere of a brain of a subject exposed to one or more of an advertisement or entertainment, and the first frequency band and the second frequency band being respectively representative of brain activity occurring at a same time;
a processor configured to:
determine a coordination between the first neuro-response data and the second neuro-response, wherein the coordination includes a measure of asymmetry between the first frequency band and the second frequency band, the asymmetry identified by:
detecting a first amplitude of the first frequency band;
detecting a second amplitude of the second frequency band; and
comparing the first amplitude and the second amplitude to determine a difference between the first amplitude of the first frequency band and the second amplitude of the second frequency band; and
assign an asymmetry value to the relationship between the first frequency band and the second frequency band based on the difference between the first amplitude of the first frequency band and the second amplitude of the second frequency band;
a response integrator comprising a processor configured to combine the asymmetry value and data representative of a first attribute of the first advertisement or entertainment to generate selection information; and
a selector to select a second advertisement or entertainment for presentation to the subject based on the selection information and data representative of a second attribute of the second advertisement or entertainment.

2. The system of claim 1, wherein the first neuro-response data includes one or more of central nervous system, autonomic nervous system data or effector data.

3. The system of claim 1, wherein the first neuro-response data is representative of at least one of attention, emotion or memory retention.

4. The system of claim 1, wherein the first advertisement or entertainment is to be delivered via a first media channel and the second advertisement or entertainment is to be delivered via a second media channel.

5. The system of claim 1, wherein the first entertainment is an electronic game having default levels and choices and the second entertainment is the electronic game having custom levels and choices.

6. The system of claim 1, wherein the first advertisement or entertainment is a media stream having a default message and the second advertisement or entertainment is the media stream having a personalized message.

7. The system of claim 1, wherein the first neuro-response data and the second neuro-response data are obtained from a first modality, the data collector is to obtain third neuro-response data from a second modality different than the first modality, and the response integrator is to generate the selection information based on the third neuro-response data.

8. The system of claim 7, wherein the response integrator is to one or more of align or combine the third neuro-response data with at least one of the first neuro-response data or the second neuro-response data.

9. The system of claim 8, wherein the response integrator is to one or more of time shift or phase shift one or more of the first neuro-response data, the second neuro-response data or the third neuro-response data to align the third neuro-response data with at least one of the first neuro-response data or the second neuro-response data.

10. The system of claim 7, wherein the third neuro-response data includes one of galvanic skin response data, electrocardiogram data, pupilary dilation data eye tracking data or electrooculography data.

11. The system of claim 1, wherein the first frequency band and the second frequency band are different.

12. A method, comprising:
obtaining first neuro-response data from a first frequency band measured in a first hemisphere and second neuro-response data from a second frequency band measured in a second hemisphere of a brain of a subject exposed to one or more of an advertisement or entertainment, and the first frequency band and the second frequency band being respectively representative of brain activity occurring at a same time;
determining a measure of asymmetry between the first frequency band and the second frequency band, the asymmetry determined by:
detecting a first amplitude of the first frequency band;
detecting a second amplitude of the second frequency band; and
determining a difference between the first amplitude of the first frequency band and the second amplitude of the second frequency band;
assigning an asymmetry value to the relationship between the first frequency band and the second frequency band based on the difference between the first amplitude of the first frequency band and the second amplitude of the second frequency band;
using a processor to combine the asymmetry value and data representative of a first attribute of the first advertisement or entertainment to generate selection information; and
selecting a second advertisement or entertainment for presentation to the subject based on the selection information and data representative of a second attribute of the second advertisement or entertainment.

13. The method of claim 12, wherein the first neuro-response data includes one or more of central nervous system, autonomic nervous system data or effector data.

14. The method of claim 12, wherein the first neuro-response data is representative of at least one of attention, emotion or memory retention.

15. The method of claim 12, wherein the first advertisement or entertainment is to be delivered via a first media channel and the second advertisement or entertainment is to be delivered via a second media channel, the first and second advertisements being otherwise identical.

16. The method of claim 12, wherein the first entertainment is an electronic game having default levels and choices and the second entertainment is the electronic game having custom levels and choices.

17. The method of claim 12, wherein the first advertisement or entertainment is a media stream having a default message and the second advertisement or entertainment is the media stream having a personalized message.

18. The method of claim 12 wherein the first neuro-response data and the second neuro-response data are obtained from a first modality and further comprising:
obtaining third neuro-response data from a second modality different than the first modality; and
generating the selection information based on the first, second and third neuro-response data.

19. A tangible machine readable storage device or disc comprising machine readable instructions thereon which, when read, cause a machine to at least:
determine a measure of asymmetry between a first frequency band and a second frequency band of neuro-response data, the first frequency band measured in a first hemisphere of a brain of a subject exposed to one or more of an advertisement or entertainment, and the second frequency band measured in a second hemisphere of the brain, and the first frequency band and the second frequency band being respectively representative of brain activity occurring at a same time, the asymmetry identified by:
detecting a first amplitude of the first frequency band;
detecting a second amplitude of the second frequency band; and
determining a difference between the first amplitude of the first frequency band and the second amplitude of the second frequency band;
assign an asymmetry value to the relationship between the first frequency band and the second frequency band based on the difference between the first amplitude of the first frequency band and the second amplitude of the second frequency band;
combine the asymmetry value and data representative of a first attribute of the first advertisement or entertainment to generate selection information; and
select a second advertisement or entertainment for presentation to the subject based on the selection information and data representative of a second attribute of the second advertisement or entertainment.

20. The machine readable device or disc of claim 19, wherein the first neuro-response data includes one or more of central nervous system, autonomic nervous system data or effector data.

21. The machine readable device or disc of claim 19, wherein the first neuro-response data is representative of at least one of attention, emotion or memory retention.

22. The machine readable device or disc of claim 19, wherein the first neuro-response data and the second neuro-response data are obtained from a first modality and further causing the machine to:
obtain third neuro-response data from a second modality different than the first modality; and
generate the selection information based on the first, second and third neuro-response data.

23. The machine readable device or disc of claim 22, wherein the third neuro-response data includes one of galvanic skin response data, electrocardiogram data, pupilary dilation data eye tracking data or electrooculography data.

* * * * *